(12) United States Patent
Anderson, Jr. et al.

(10) Patent No.: US 6,362,880 B1
(45) Date of Patent: Mar. 26, 2002

(54) LOW TEMPERATURE ADAPTOR FOR EVAPORATIVE LIGHT DETECTION

(75) Inventors: James M. Anderson, Jr., Arlington Heights; Raaidah Saari-Nordhaus, Lindenhurst; Bart C. Benedict, Arlington Hts; Melissa Wilcox, Libertyville; Ronald Krob, Chicago, all of IL (US); Arnold Williams, Boulder, CO (US)

(73) Assignee: Alltech Associates, Inc., Deerfield, IL (US)

( * ) Notice: Subject to any disclaimer, the term of this patent is extended or adjusted under 35 U.S.C. 154(b) by 0 days.

(21) Appl. No.: 08/932,262

(22) Filed: Sep. 17, 1997

(51) Int. Cl.[7] ............................................... G01N 15/06
(52) U.S. Cl. ...................................... 356/337; 356/37
(58) Field of Search ................................ 356/338, 339, 356/336, 36, 37, 337; 210/656, 198.2

(56) References Cited

U.S. PATENT DOCUMENTS 4,958,529 A * 9/1990 Vestal ......................... 250/288
5,807,750 A * 9/1998 Baum et al. ................. 436/164

OTHER PUBLICATIONS

"New! Alltech 500 ELSD—Your Best Choice For Solving Tough Detection Problems"—Bulletin ™338A, Alltech Associates, Inc., Deerfield, IL.

"Sedex 55: Evaporative Light Scattering Detector Instruction Manual", Sedere, ANVAR–University of Orléans, France.

DDL 31 User's Instruction Manual: Version 2.0 (GB) Sep., 1996, EUROSEP Instruments, France.

* cited by examiner

Primary Examiner—F. L. Evans
Assistant Examiner—Tu T. Nguyen
(74) Attorney, Agent, or Firm—Brinks Hofer Gilson & Lione

(57) ABSTRACT

The present invention is directed to a system for converting between single flow and split flow evaporative light scattering detection devices for detecting samples in a mobile phase. Included in the system is a evaporative light scattering detection device, a low temperature adaptor, and a connection tube for providing a fluid connection between the evaporative light scattering detection device and the low temperature adaptor.

9 Claims, 15 Drawing Sheets

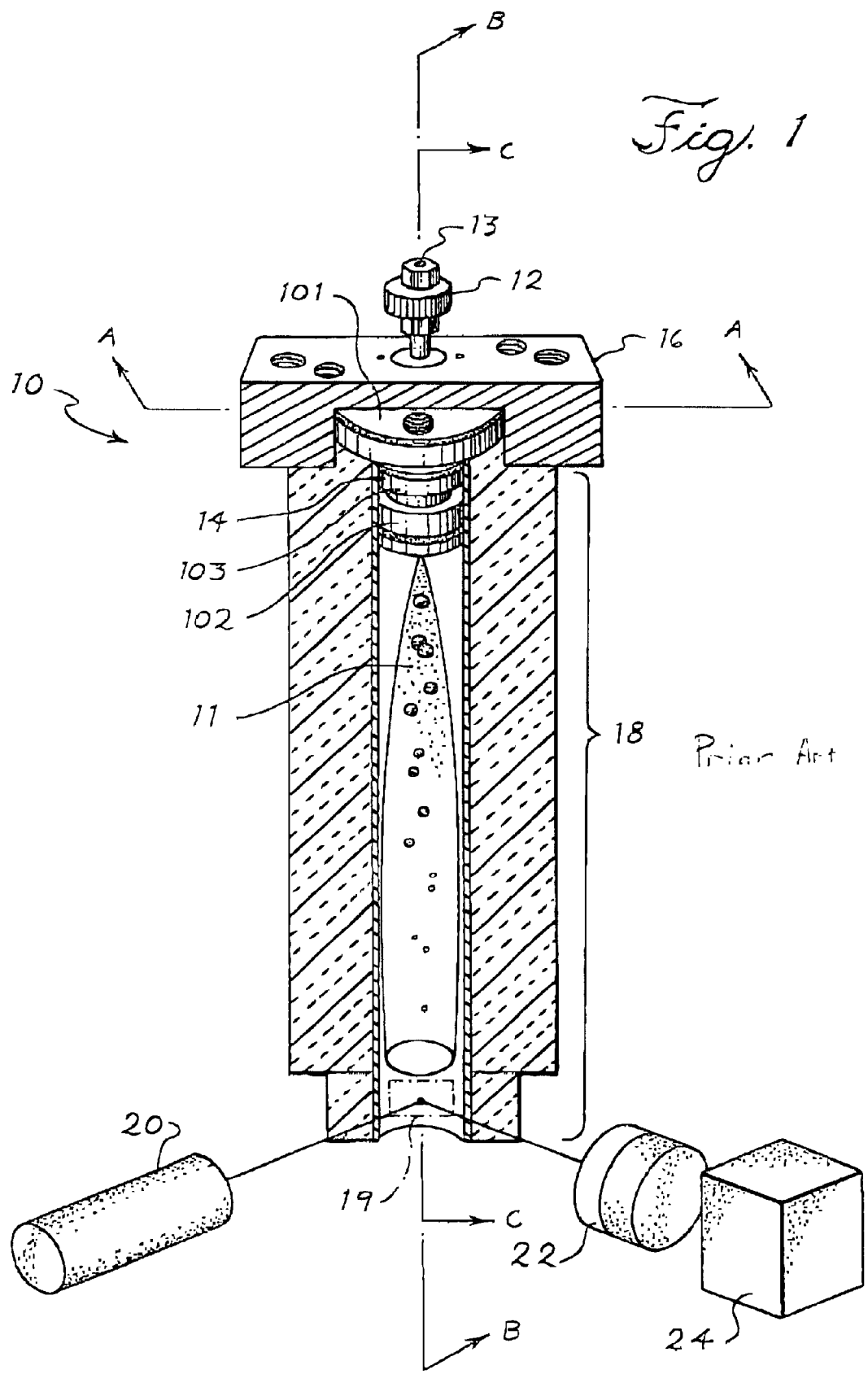

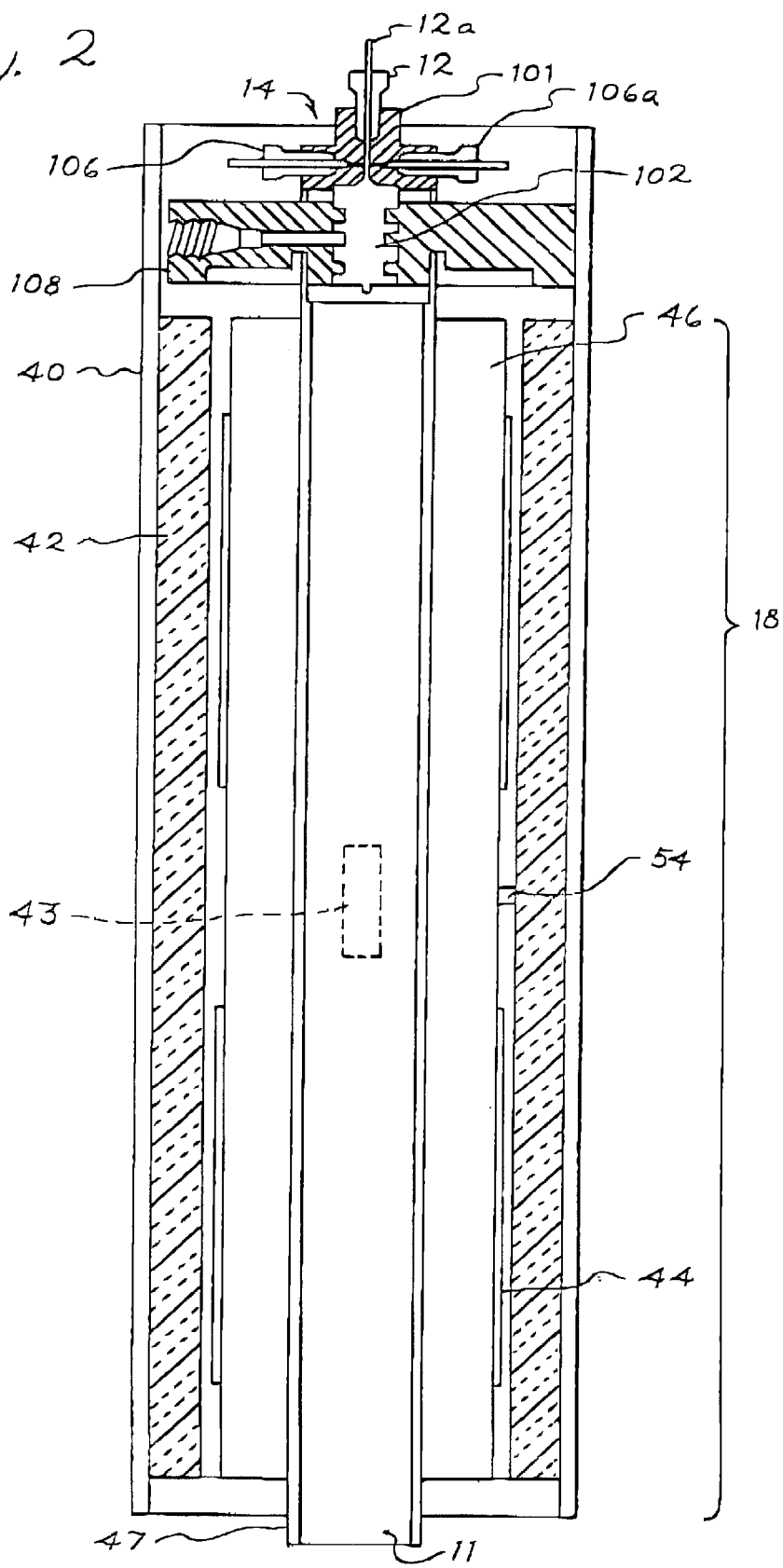

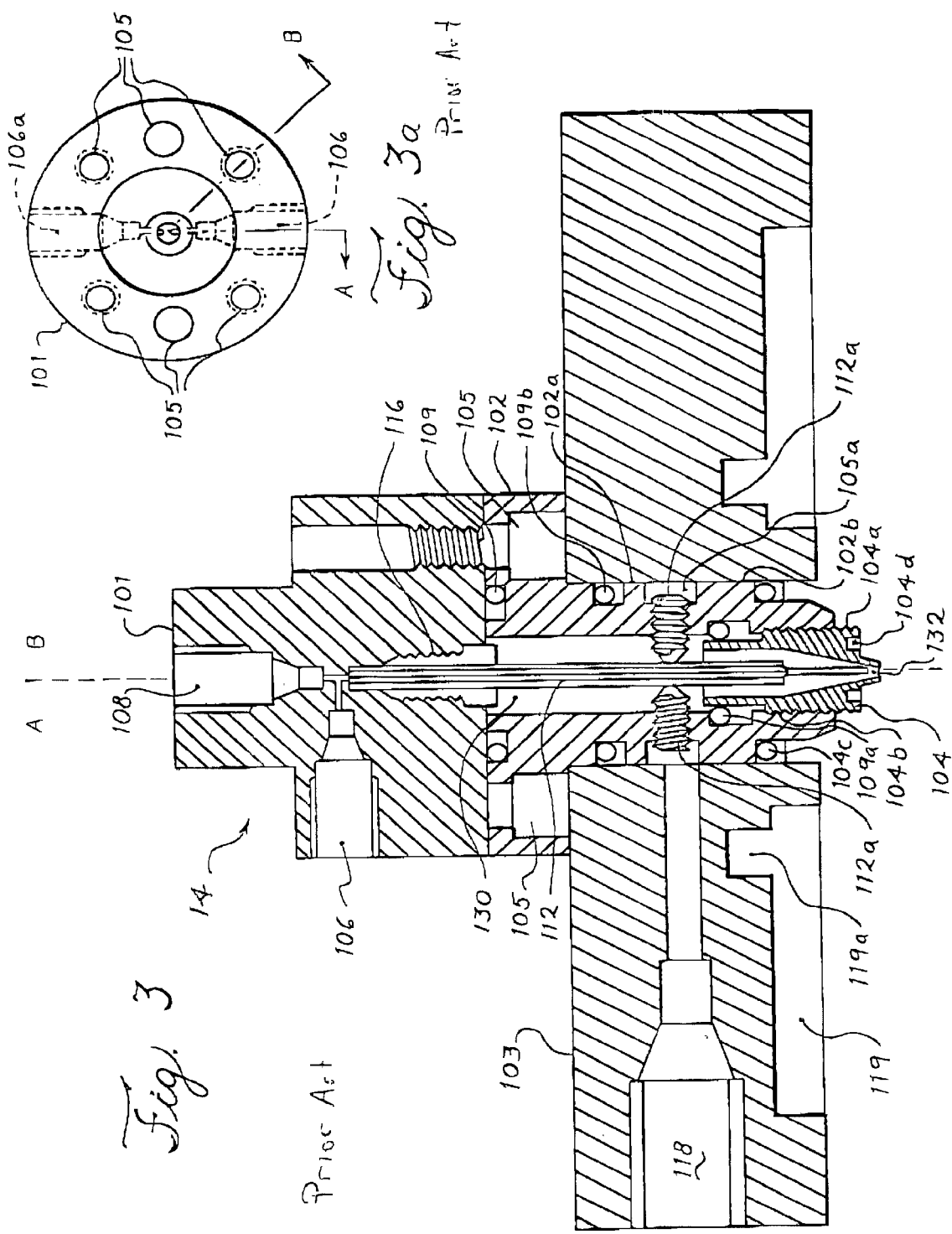

① VITAMIN A
② VITAMIN E
③ VITAMIN K₁

① LAURIC ACID
② MYRISTIC ACID
③ PENTADECYLLIC ACID
④ PALMITIC ACID

① LAURIC ACID
② MYRISTIC ACID
③ PENTADECYLLIC ACID
④ PALMITIC ACID

① FRUCTOSE
② GLUCOSE
③ SUCCOSE
④ MALTOSE
⑤ LACTOSE

① CHOLESTEROL (150 μg/mL)
② PALMITIC ACID (250 μg/mL)
③ PHOSPHATIDYLETHANOLAMINE (150 μg/mL)
④ PHOSPHATIDYLSERINE (300 μg/mL)
⑤ PHOSPHATIDYLCHOLINE (150 μg/mL)
⑥ SPHINGOMYELIN (150 μg/mL)

LOW TEMPERATURE ADAPTOR FOR EVAPORATIVE LIGHT DETECTION

FIELD OF THE INVENTION

Applicants' invention is directed to the field of evaporative light scattering detection and methods.

BACKGROUND OF THE INVENTION

Evaporative light scattering detection is a method of detecting samples that have been previously separated in various chromatography methods such as, for example, High Performance Liquid Chromatography (HPLC), Gel-Permeation Chromatography (GPC), High Performance Centrifugal Partition Chromatography (HPCPC), Field Flow Fractionation (FFF), and Supercritical Fluid Chromatography (SFC). Evaporative light scattering detection is preferably used when the sample components (e.g., components to be detected) have lower volatility than the mobile phase. A wide variety of sample types can be detected in evaporative light scattering detection. Such sample types include, for example, lipids, triglycerides, surfactants, polymers, underivatized fatty and amino acids, carbohydrates and pharmaceuticals.

Generally, evaporative light scattering detection involves four main steps: 1) nebulization of the chromatography effluent, (which consists of the mobile phase and the sample), into an aerosol of particles, 2) evaporation of the mobile phase, 3) light scattering by the sample particles, and 4) detection of the scattered light. There are two principal types of devices used in evaporative light scattering detection known in the art. In the first type (the "single flow" design), the nebulized chromatography effluent is immediately introduced into a heated drift tube where the mobile phase is evaporated. The sample particles are then flowed from the heated drift tube to an optical cell where light scattering and detection occurs. One such example of this type of device (the Alltech Model 500 ELSD) is sold by the assignee of this application, ALLTECH ASSOCIATES, INC. Details concerning the design and operating parameters for such a device are disclosed in the Operating Manual for the Alltech Model 500 ELSD, which is incorporated herein by reference.

In the second type of device, (the "split-flow" design), the nebulized chromatography effluent is first flowed through a nebulization chamber before entering the heated drift tube. In the nebulization chamber, the nebulized chromatography effluent is split, namely, the larger droplets are eliminated by condensation/impaction on the walls of the nebulization chamber. This condensate is drained to waste. Only the smaller nebulized droplets are subsequently flowed to the drift tube where the mobile phase (which is now free of the larger droplets) is more easily evaporated. Thereafter, the sample particles are flowed to the optical cell for light scattering and detection. Devices of this design type are available from, for example, SEDERE or EUROPSEP INSTRUMENTS.

The above-described design types have particular advantages depending on the mobile phase and the sample type. The single flow design is preferred for use in applications involving relatively non-volatile sample types and volatile organic mobile phases. Because all of the sample enters the optical cell in this design, response and sensitivity is maximized.

However, the split-flow design is preferably used with highly aqueous mobile phases and semi-volatile sample types. Highly aqueous mobile phases generally require higher evaporation temperatures. If the sample is volatile at these higher evaporation temperatures, sample loss is incurred during the evaporation step resulting in poorer sensitivity. By using the split-flow design, the evaporation temperature is reduced. This is accomplished by removing the larger mobile phase droplets in the nebulized chromatography effluent before the evaporation step. By removing the larger droplets, a smaller and more uniform particle size distribution is achieved in the mobile phase, which leads to lower evaporation temperatures. The lower evaporation temperatures, in turn, lead to less sample loss during the evaporation step. However, for non-volatile sample types and organic mobile phases, the split-flow design is generally less preferred because some of the non-volatile sample may be lost during the splitting of the chromatography effluent.

Another problem with devices of the split-flow design is that the split ratio of the sample (i.e., the amount that goes to waste versus the amount that is ultimately detected) is affected by, among other things, the laboratory temperature. In other words, fluctuations in laboratory temperatures lead to fluctuations in droplet size in the nebulized chromatography effluent. Thus, as ambient and/or laboratory temperatures fluctuate, the split ratio and corresponding reproducibility of sample detection may vary from run to run.

As is evident from the above-discussion, depending on the mobile phase and the sample type being detected, one evaporative light scattering detection design and method is advantageous over the other. However, laboratories often work with both aqueous and organic mobile phases and various sample types with different volatilities. Ideally, laboratories would have available both design types for evaporative light scattering detection. However, in order to have this benefit, the laboratory would need to purchase two separate devices, which can be expensive. It would be advantageous and constitute an improvement in the art if an evaporative light scattering detection device and system were developed which could be quickly and inexpensively converted between the single flow and split flow designs. Applicants have developed such a device and system. Moreover, with respect to the split-flow design, Applicants invention addresses the problem of the variation in split ratio caused by fluctuating laboratory temperatures.

SUMMARY OF THE INVENTION

In one respect, the present disclosure is directed to a system for evaporative light scattering detection which allows for quick and easy conversion between a single flow design and a split flow design, depending on the mobile phase and sample types to be detected. The system includes an evaporative light scattering detection device comprising a removably attached nebulizer in fluid communication with a heated drift tube, a light source, and a detector for detecting scattered light. The system also includes a low temperature adaptor comprising a nebulization chamber and a coil. The system further includes a connection tube for providing a fluid connection between the light scattering detection device and the low temperature adaptor for converting from a single flow to the split flow designs. One end of the connection tube is attached to the low temperature adaptor and the other end of the connection tube is removably attached to the evaporative light scattering detection device such that the connection tube provides fluid communication between the low temperature adaptor and the evaporative light scattering device. The low temperature adaptor is connected to the evaporative light scattering device by first removing the nebulizer from the detection device and attaching in its place the connection tube to provide fluid communication between the low temperature adaptor and the detection device. The low temperature adaptor further comprises a nebulizer. The nebulizer for the low temperature adaptor may be the nebulizer removed from the evaporative light scattering device or a second nebulizer.

The low temperature adapter in the above system further preferably comprises a sweep gas channel for introducing into the nebulization chamber sweep gas independently of the nebulizing gas. The sweep gas is for assisting in the evaporation of the mobile phase. Also, heat tape is preferably affixed to the nebulization chamber and the coil of the low temperature adaptor in the above system at pre-determined intervals for controlling the temperature of the nebulization chamber and coil.

In another respect, the disclosure is directed to a low temperature adaptor for a light scattering detection device which reduces the temperature required to evaporate the mobile phase. The low temperature adaptor is especially preferred for aqueous mobile phases and semi-volatile sample types. The low temperature adaptor comprises a nebulization chamber, a coil and a connection tube for removably attaching the low temperature adaptor to the evaporative light scattering detection device such that the connection tube provides a fluid connection between the low temperature adaptor and the evaporative light scattering detection device. Heat tape is preferably affixed to the nebulization chamber and the coil at pre-determined intervals for controlling the temperature of the nebulization chamber and coil. The low temperature adaptor preferably further includes a sweep gas channel for introducing sweep gas into the nebulization chamber independently of nebulizing gas. Finally, the low temperature adapter further includes a nebulizer. The nebulizer may be the nebulizer removed from the evaporative light scattering detection device prior to connecting the low temperature adapter or a second nebulizer.

In another aspect, the disclosure concerns a method of evaporative light scattering detection which is substantially resistant to fluctuations in ambient temperature conditions. By substantially resistant to fluctuations in ambient temperature conditions, it is meant that the detection device of this invention provides consistent detection when laboratory temperatures fluctuate of from about 15° C. to about 40° C. The method comprises flowing nebulized chromatography effluent comprising mobile phase and sample to be detected through a nebulization chamber, wherein the temperature of the nebulization chamber is controlled by a heat source; reducing the particle size distribution of the nebulized chromatography effluent in the nebulization chamber; evaporating the mobile phase; and detecting the sample by evaporative light scattering detection. Preferably, the temperature in the nebulization is controlled by heat tape affixed to the nebulization chamber at predetermined intervals.

DESCRIPTION OF THE DRAWINGS

FIG. 1 is a schematic diagram illustrating the principles of operation of an evaporative light scattering detection device.

FIG. 2 is a cross-section view along line A—A of FIG. 1 showing the drift tube assembly.

FIG. 3 is a cross-section along lines A—A and B—B of FIG. 1 of the nebulizer and nebulizer adaptor.

FIG. 3a is a top view of the nebulizer and nebulizer adaptor shown in FIG. 3.

FIG. 8a is a partial cross-section view along line A—A of FIG. 6 showing the attachment of the nebulizer union to the nebulization chamber of the low temperature adaptor.

FIG. 8b is a cross-section view along lines A—A and C—C of FIG. 6.

FIG. 8c is a top plan view of FIG. 8a.

DETAILED DESCRIPTION OF THE PREFERRED EMBODIMENTS

Figure 1A:
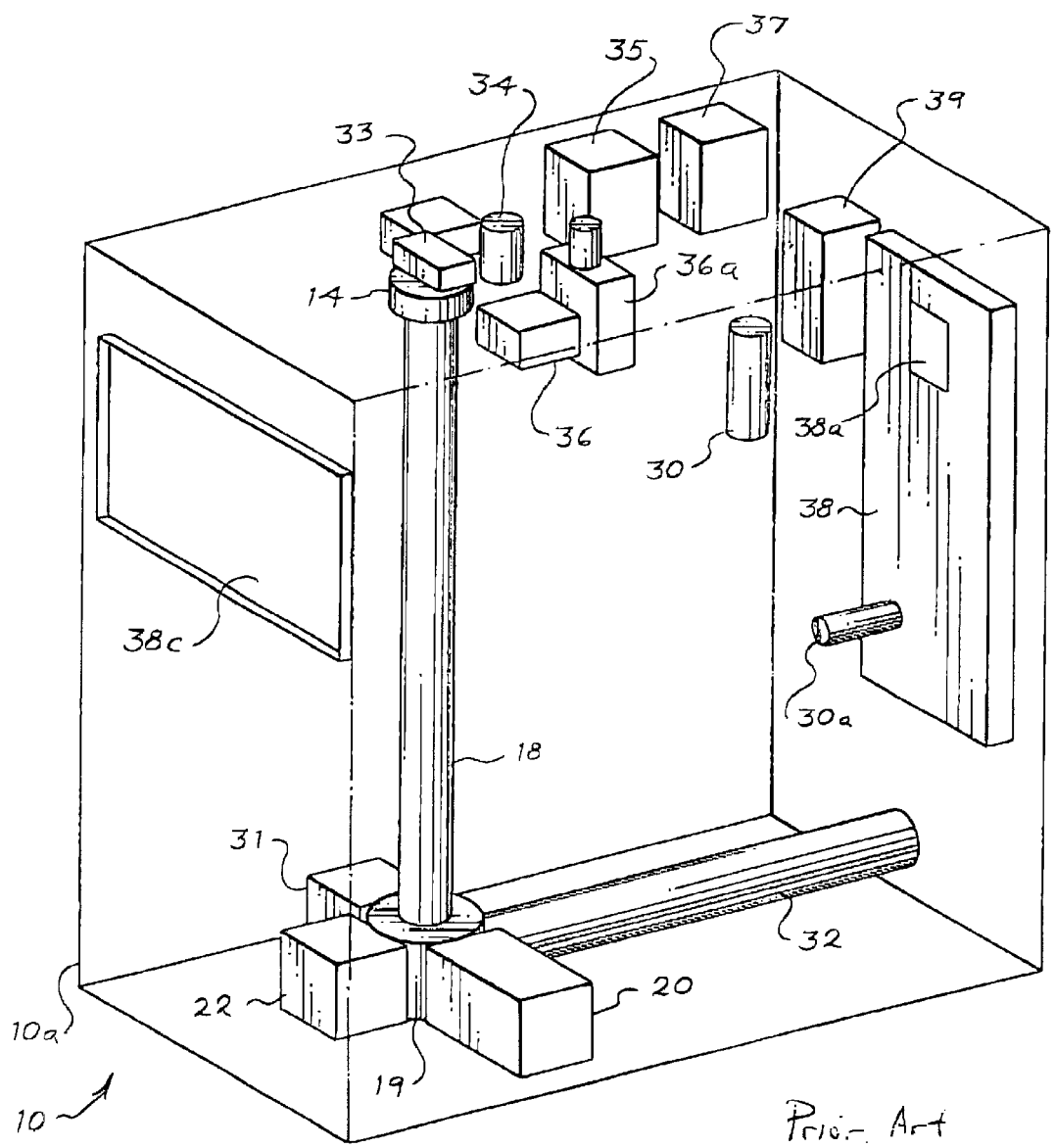
FIG. 1a is an isometric view of the configuration for an evaporative light scattering detection device.

FIGS. 1–4 illustrate an evaporative light scattering detection device of the single flow design. FIG. 1 provides an overview of the principal of operation of an evaporative light scattering detection device 10. The scattering device 10 has a connector 12. The connector 12 provides a fluid connection between the chromatography column (not shown) and the evaporative light scattering device 10. The connector 12 is preferably made from stainless steel and is threadingly engaged to nebulizer bracket 16. Chromatography effluent is flowed into the evaporative light scattering device 10 through channel 13 in connector 12. Nebulizer bracket 16 removably attaches nebulizer 14 (which consists of pieces 101, 102 and 103 discussed below) to drift tube assembly 18. The nebulizer 14 contains a nebulizer needle (not shown). The drift tube assembly 18 surrounds a central heated drift tube channel 11. Finally, a laser light source 20, a photodetector 22 and amplifier 24 are provided.

In operation, and with reference to FIG. 1, the chromatography effluent is flowed through connector 12 to nebulizer 14. The chromatography effluent is directed through the nebulizer needle (not shown). Upon exiting the nebulizer needle, the chromatography effluent is impacted by nebulizing gas to form an aerosol of droplets, preferably of generally uniform size. The nebulizing gas may include any gas that is inert to the sample such as helium, carbon dioxide, air or nitrogen, and is preferably nitrogen.

The nebulized chromatography effluent is then flowed through channel 11 in the drift tube assembly 18. In channel 11, the mobile phase is evaporated leaving behind the non-volatile sample particles. The non-volatile sample particles are flowed through channel 11 to the light scattering zone 19 for detection. A light source 20 emits light, which the sample particles scatter. The scattered light is then detected at the photodetector 22. The photodetector 22 then produces a signal which is sent to an amplifier 24 though analog outputs in the photodetector.

The light source 20 is preferably a Class IIIA laser product with a 650 nm laser diode, 5 mW maximum power, collimating optics, and polarized. A preferred laser light source is available from COHERENT, as part no. VLM3-5L. The photodetector 22 is preferably made from a silicon photodiode. A preferred photodetector 22 is available from HAMAMATSU, as part no. S2386-8K. The photodetector 22 is preferably located at a 90 degree angle from the light source 20. A light trap 31 is also preferably located at an 180 degree angle from the light source 20 to collect any light not scattered by the sample particles in the aerosol stream. After detection in the detection zone, the sample particles are flowed through an exhaust line (now shown) to waste. Preferably the exhaust is flowed to a fume hood or other ventilation device located close to the detector to remove the detector exhaust from the laboratory.

A configuration and preferred flow paths for the sample and the nebulizing gas of an evaporative light scattering device 10 is illustrated by FIG. 1a. Preferably included in the evaporative light scattering device 10 is liquid pressure sensor 33, liquid back pressure relief valve 34, gas shut off valve 35, mass flow sensor 36 and mass flow control 36a, gas pressure sensor 37, temperature control 38a, power input 39, logic board 38 (which includes a microprocessor) and front control panel 38c. The logic board 38 is in electrical communication (not shown) with front panel display 38c.

The liquid back pressure relief valve 34 is in fluid communication with the nebulizer 14 via a stainless steel flow path (not shown). If the nebulizer needle becomes blocked or chromatography effluent back pressure otherwise exceeds a pre-determined level, the back pressure relief valve 34 diverts the flow of chromatography effluent from nebulizer 14 to waste. A preferred back pressure relief valve is a diaphragm back pressure regulator available from the assignee of this application ALLTECH ASSOCIATES, INC. The liquid pressure sensor 33 is also in fluid communication with the nebulizer 14 via a stainless steel flow path (not shown). The liquid pressure sensor monitors the chromatography effluent back pressure in the nebulizer 14. The liquid pressure sensor 33 is also in electrical communication (not shown) with logic board 38 and communicates pressure readings to logic board 38 for display on front panel 38c. A preferred liquid pressure sensor is available from KELLER PSI, as part no. PR-6–10. The sample in the chromatography effluent is flowed from nebulizer 14 through drift tube assembly 18 to detection zone 19 for sample detection.

The nebulizing gas is flowed from gas inlet 30a to gas filter 30 where impurities are removed from the nebulizing gas. A preferred gas filter has a 1 micron pore size and is available from WEBSTER ASSOC., as part no. FILN05012YE. The nebulizing gas is then flowed from gas filter 30 through, respectively, gas pressure sensor 37, gas shut-off valve 35, mass flow controller 36a, mass flow sensor 36 to nebulizer 14. Each of the foregoing devices are in gas communication via TEFLON tubing. The gas pressure sensor 37 monitors the nebulizing gas and is in electrical communication with logic board 38. The gas pressure sensor 37 triggers an alarm if the nebulizing gas pressure falls below or exceeds pre-determined levels. A preferred gas pressure sensor is available from IC SENSORS, as part no. 1201A-100G-3L. The gas shut-off valve 35 is in electrical communication with logic board 38 and may be triggered to stop the flow of nebulizing gas as, for example, between detection runs. The mass flow controller 36a is manually operated for setting the flow rate of the nebulizing gas. A preferred mass flow controller allows for nebulizing gas flowrates of from 0–5 Standard Liters Per Minute (SLPM) and is available from CONDYNE, as part no. 100–6(14)4. The mass flow sensor 36 measures the flow rate of the nebulizing gas and is in electrical communication with logic board 38, which in turn displays the nebulizing gas flowrate on front control panel 38c. A preferred mass flow sensor is available from INTEGRATED ELECTRONICS, as part no. AWM43600V.

The logic board 38 further processes the analog signal from the photodetector 22 and contains a microprocessor for displaying readings from the mass flow sensor on an LCD (not shown) on the front panel 38c. Preferably, each of the foregoing components are contained within the same housing 10a.

In operation, the nitrogen nebulizing gas is preferably regulated from 45–80 psig with 99.9% purity or better. A stable gas flowrate and pressure are necessary for reproducible results. The gas is preferably free of contaminants, such as oil, water, particulate or any other non-volatile substances. The droplet size in the nebulized chromatography effluent may be regulated by varying the flow rate of either the chromatography effluent and/or the nebulizing gas. The lower the flow rate of the chromatography effluent, the less gas and heat necessary for nebulization and subsequent evaporation.

Figure 3B:
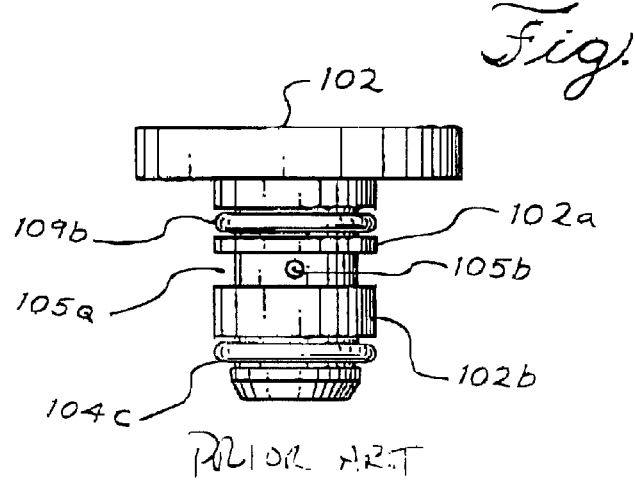
FIG. 3b is a side view of the nebulizer body portion of the nebulizer shown in FIG. 3.
Figure 4:
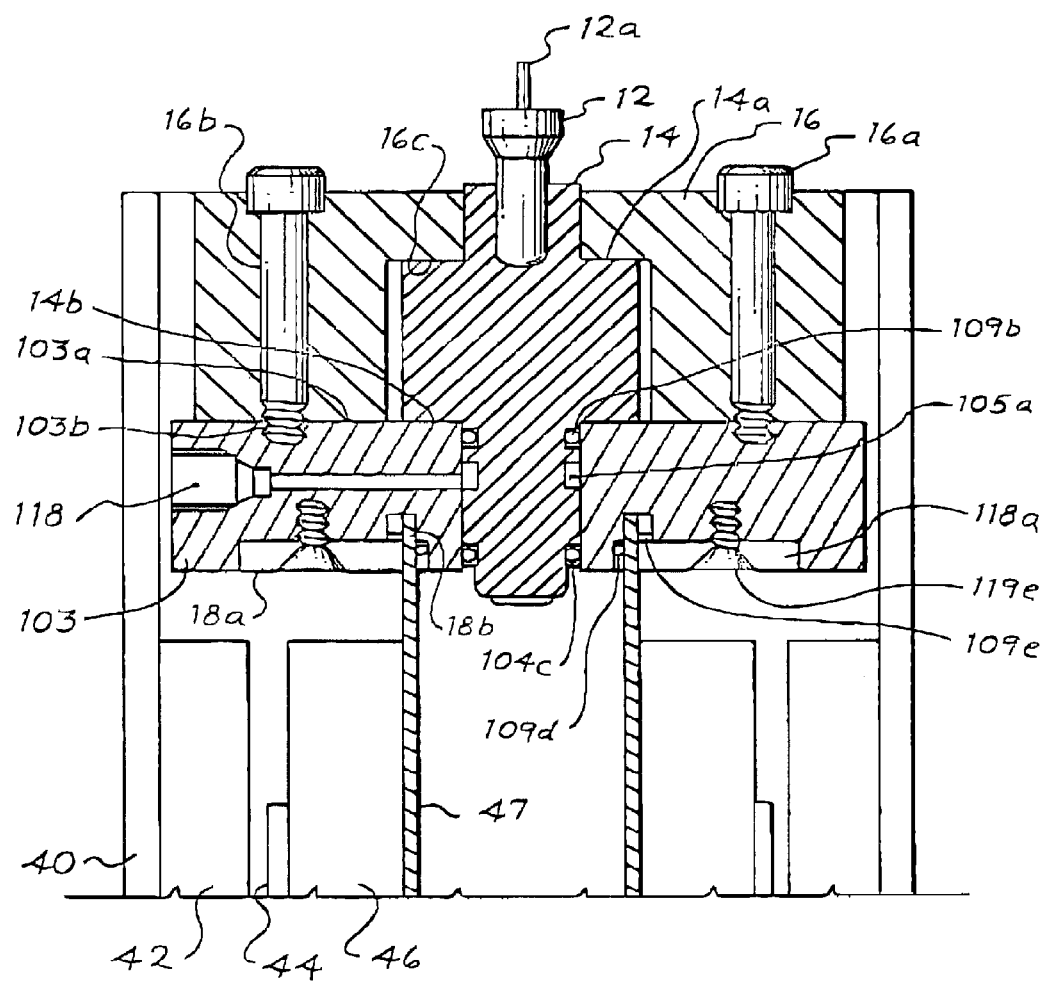
FIG. 4 is a cross-section view along line A—A of FIG. 1 showing the manner of connecting the nebulizer to the drift tube assembly.

FIGS. 2, 3 and 4 and illustrate the construction of the nebulizer 14 and the drift tube assembly 18 in more detail. The drift tube assembly 18 comprises four phenolic cover plates 40 surrounding insulation 42. The insulation 42 is preferably ½ inch polyimide available from McMASTER CARR, as part no. 446K121. The insulation 42, in turn, surrounds surface heaters 44. The surface heaters are thermoelectric heating elements preferably of silicon pad style available from WATLOW, as part no. F030050C7. The surface heaters are preferably mounted by an appropriate adhesive on heating tube 46. Heating tube 46 is preferably made from aluminum or other appropriate thermally conductive material. A drift tube 47 is telescopically positioned by a slip fit within heating tube 46. The drift tube 47, which surrounds channel 11, is preferably constructed from stainless steel. A thermal fuse 43 (shown in phantom) is preferably provided for turning the heat off if temperature exceeds a pre-determined limit. The fuse is in electrical communication with the power source for the silicon heaters 44. Also preferably included is temperature sensor 54 for monitoring the temperature in the drift tube assembly 18. The sensor is in electrical connection with logic board.

With reference to FIGS. 3, 3a and 3b, the nebulizer 14 comprises a nebulizer tee nozzle 101, a nebulizer body 102, nebulizer adaptor 103, and tip piece 104. The nebulizer body 102 is attached to tee nozzle 101 by bolts 105. Preferably, six bolts 105 are provided (see FIG. 3a). The adaptor 103 is removably secured to the drift tube assembly 18 (see FIG. 4). The tee nozzle 101, nebulizer body 102 and nebulizer adaptor 103 are preferably made from stainless steel. O-rings 109, 109a and 109b are provided to give a liquid and air tight seal between the tee nozzle 101, nebulizer body 102, and nebulizer adaptor 103. O-rings 109, 109a and 109b are VITON O-rings available from DUPONT. Bottom seal 104c provides a gas and liquid seal between body 102 and adapter 103. Bottom seal 104c is preferably a teflon/SS seal available from VERI-SEAL as part no. W10-MH-P-012-X-1. The tip piece 104 is removably secured to nebulizer body 102 by threads 104a and complementary threads 104b. Openings 104d are provided in tip 104 for receiving a two-pronged adjustment tool which assists in adjusting tip 104 relative to nebulizer body 102.

A chromatography effluent port 108 is provided for introducing and flowing the chromatography effluent into the nebulizer 14 and to nebulizer needle 112. Chromatography effluent port is in fluid communication with connector 12 (see FIG. 2) by a standard nut and ferrule connection. A back pressure channel 106 is also provided which is in fluid communication with liquid back pressure relief valve 34 (see FIG. 1a). A liquid pressure sensor channel 106a (see FIG. 3a) is also provided which is in fluid communication with liquid pressure sensor 33 (see FIG. 1a). If chromatography effluent back pressure in the nozzle exceeds a predetermined limit, the liquid back pressure relief valve diverts chromatography effluent flow away from the nebulizer through liquid back pressure relief valve 34 to waste. Channels 106 and 106a are in fluid connection with, liquid back pressure relief valve and liquid pressure sensor, respectively, by stainless steel tubing connected to channels 106 and 106a by standard nut and ferrule connections available from ALLTECH as part nos. 206085 (nut) 286075 (ferrule).

The nebulizer needle 112 comprises two concentrically positioned needles which have been silver soldered to each other. Preferably, there is no void between the concentrically positioned needles. The nebulizer needle 112 has a longitudinal channel through which the chromatography effluent is flowed. The nebulizer needle 112 is preferably constructed from stainless steel. The nebulizer needle 112 is maintained in fluid connection with chromatography effluent port 108 by nut 116. Nut 116 has a longitudinal bore in which nebulizer needle 112 sits. Preferably, the internal diameter of the nebulizer needle is between about 0.007 to about 0.012 of an inch.

The nebulizer body further comprises set screws 112a for centering the nebulizer needle 112. It is important to center the nebulizer needle so that the chromatography effluent exiting the needle is substantially in the concentric center of the nebulizing gas. The pressurized nebulizing gas is introduced into the nebulizer through nebulizing gas port 118 in nebulizer adaptor 103. The nebulizer gas flows into channel 105*a* formed between nebulizer adaptor 103 and shoulders 102*a* and 102*b* of nebulizer body 102. A small opening 105*b* is formed in the nebulizer body 102 generally in the plane of the set screws 112*a* (see FIG. 3*b*). The pressurized nebulizing gas flowing through opening 105*b* is forced into nebulizing gas chamber 130. Because seal 109*a* provides a gas tight seal, the pressurized nebulizing gas is forced inside tip 104 into nebulizing zone 132. The nebulizing gas strikes the chromatography effluent exiting the nebulizer needle 112 in the nebulizing zone 132. The nebulizing gas breaks-up the chromatography effluent to form an aerosol of droplets. The chromatography effluent aerosol is then flowed to the drift tube assembly 18 for the evaporation step as discussed above. In addition to set screws 112 for centering the nebulizer needle, nebulization (e.g. droplet particle size) may also be varied by adjusting tip 104.

FIGS. 3 and 4 illustrates the fluid connection between the nebulizer 14 and drift tube assembly 18. The nebulizer 14 is removably secured to the drift tube assembly 18 by operation of nebulizer bracket 16, screws 16*a*, nebulizer adaptor 103 and drift tube cap 118*a*. The nebulizer adaptor 103 has an L-shaped channel 119 for receiving the drift tube assembly 18. In particular, a terminal end 18*b* of the tube 47 of the drift tube assembly 18 is positioned in void 119*a* of channel 119. A clip 109*e* is attached to the terminal end of tube 47 to provide a shoulder for resting upon the drift tube cap 118*a*. An O-ring 109*d* provides a liquid and gas tight seal at the junction of the terminal end of tube 47 with nebulizer adaptor 103. The drift tube assembly 18 further has a drift tube cap 18*a* which fits into channel 119 of the nebulizer adaptor 103. Screws 119*e* are provided to removably secure the drift tube cap 18*a* to the nebulizer adaptor 103. Finally, nebulizer bracket 16 has channels 16*b* for receiving screws 16*a*. Shoulder 16*c* of the nebulizer bracket 16 abuts against shoulder 14*a* of nebulizer 14. Shoulder 14*b* of nebulizer 14 abuts against surface 103*a* of nebulizer adaptor 103. Thus, when screws 16*a* are inserted through channel 16*b* and into channels 103*b* formed in nebulizer adaptor 103 (not shown in FIG. 3), the nebulizer is removably secured in fluid communication with the drift tube assembly 18.

As those skilled in the art will recognize, nonvolatile impurities in the mobile phase or nebulizing gas will be detected thereby producing baseline "noise." By using the highest quality gas, solvents and volatile buffers which are preferably filtered, the baseline noise will be reduced. Baseline noise will also result from the mobile phase not being completely evaporated. Also, the sample may be volatilized if the drift tube temperature is too high or the sample is too volatile. The temperature in the heated drift tube 18 and the flowrate for the nebulizing gas are dictated by the volatility and flow rate of the mobile phase. At a mobile phase flowrate of 1 mL/min., the following drift tube temperatures (in ° C.) and nebulizing gas flowrates (in Standard Liters Per Minute (SLPM)) are recommended: acetone (45 C, 1.50); acetonitrile (70 C, 1.70); heptane (50 C, 1.60); hexane (60 C, 1.60); isopropyl alcohol (80 C, 2.20); methanol (70 C, 1.65); methylene chloride (75 C, 2.00); water (115 C, 3.20); methanol:water (90:10) (70 C, 2.00); and acetonitrile:water (75:25) (90 C, 2.00).

When calculating the starting temperature and nebulizing gas flowrate for mixed mobile phases, the above values in the same ratio as the mobile phase solvents are to each other should be used. Thus, if running a binary mobile phase of 60% methanol and 40% water, the temperature would be (0.6)(70)+(0.4)(115)=88 C. The nebulizing gas flowrate would be (0.6)(1.65)+(0.4)(3.20)=2.27 SLPM. The above recommended temperature and nebulizing gas flowrates should be adjusted if the mobile phase flowrates are changed from 1 mL/min. Lower mobile phase flowrates generally require lower nebulizing gas flowrates and temperature. On the other hand, higher mobile phase flowrates may require higher nebulizing gas flowrates and temperature.

Finally, with respect to solvents not discussed above, suitable starting drift tube temperatures and nebulizing gas flowrates may be estimated as follows. Obtain from an appropriate reference the solvent's boiling point and vapor pressure. Use the temperature and gas flowrate of the solvent listed above that most closely matches the boiling point and vapor pressure of the solvent of interest.

Of course, some experimentation may be necessary to obtain the optimum gas flowrate, mobile phase flowrate and temperature for any particular analysis. The nebulizing gas flow rate determines the mobile phase droplet size. Higher flowrates produce smaller droplet sizes which enhance vaporation. On the other hand, smaller droplets produce smaller sample particles which scatter less light and produce smaller signals for detection. Generally, the optimal nebulizing gas flowrate is the lowest flowrate that will produce the largest peaks with an acceptable, low noise baseline. This can be determined by finding the signal to noise ratio of various flowrates. By plotting the signal to noise ratio vs. peak area and/or the gas flowrate vs. peak area, the optimal gas flowrate may be determined.

With respect to the flowrate of the mobile phase, higher flowrates require higher gas flowrates and higher temperatures. It is therefore preferable to use the lowest mobile phase flowrate possible. The temperature selection depends on mobile phase volatility, and flowrate, and nebulizing gas flowrate. Aqueous solvents require higher temperatures than organic solvents. Lower nebulizing gas flowrates produce larger droplets and, therefore, require higher temperatures for evaporation. Preferably, the lowest temperature that will produce an acceptable, low noise baseline should be used. When working with temperature sensitive samples that are volatile at the temperature necessary to evaporate the mobile phase, the drift tube temperature may be decreased by increasing the nebulizing gas flowrate. However, because smaller droplets are produced, the increased gas flowrate will decrease detection sensitivity of the sample.

When it is desired to convert from the single flow design as previously described to the split-flow design, when, for example, aqueous mobile phases and semi-volatile samples are present, this conversion may be quickly and easily accomplished by using the low temperature adaptor of the present invention. To accomplish the conversion, the nebulizer bracket 16 and nebulizer 14 are removed from the nebulizer adaptor 103 by removing screws 16a and manually removing these pieces (see FIG. 4). The low temperature adaptor is inserted in place of the nebulizer 14 as described below with reference to FIG. 10. However, before discussing the manner in which the low temperature adapter is connected to the evaporative light scattering detection device, an overview of the low temperature adapter construction is provided.

Figure 5:
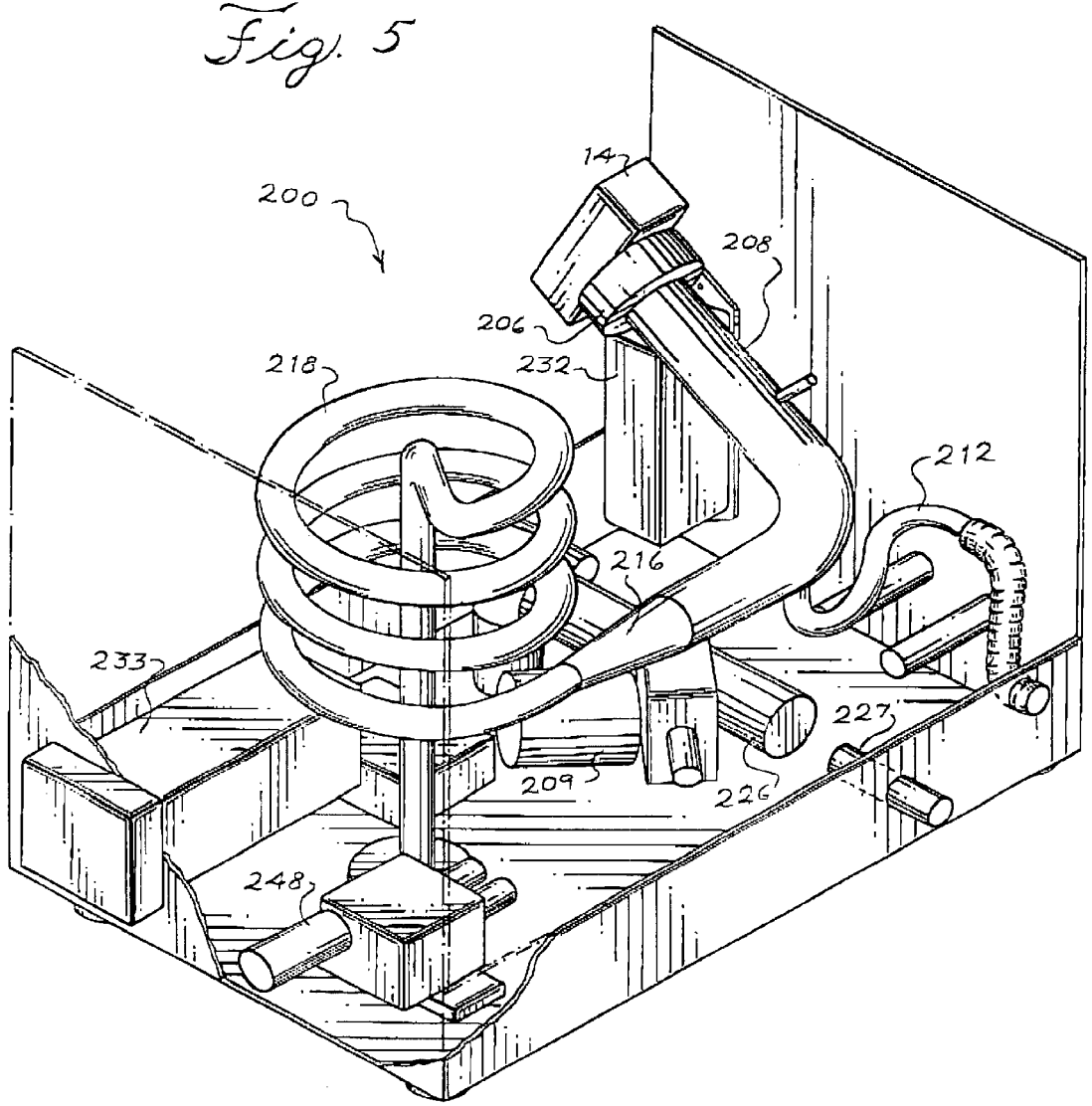
FIG. 5 is a perspective isometric view of the configuration for a low temperature adaptor.
Figure 6:
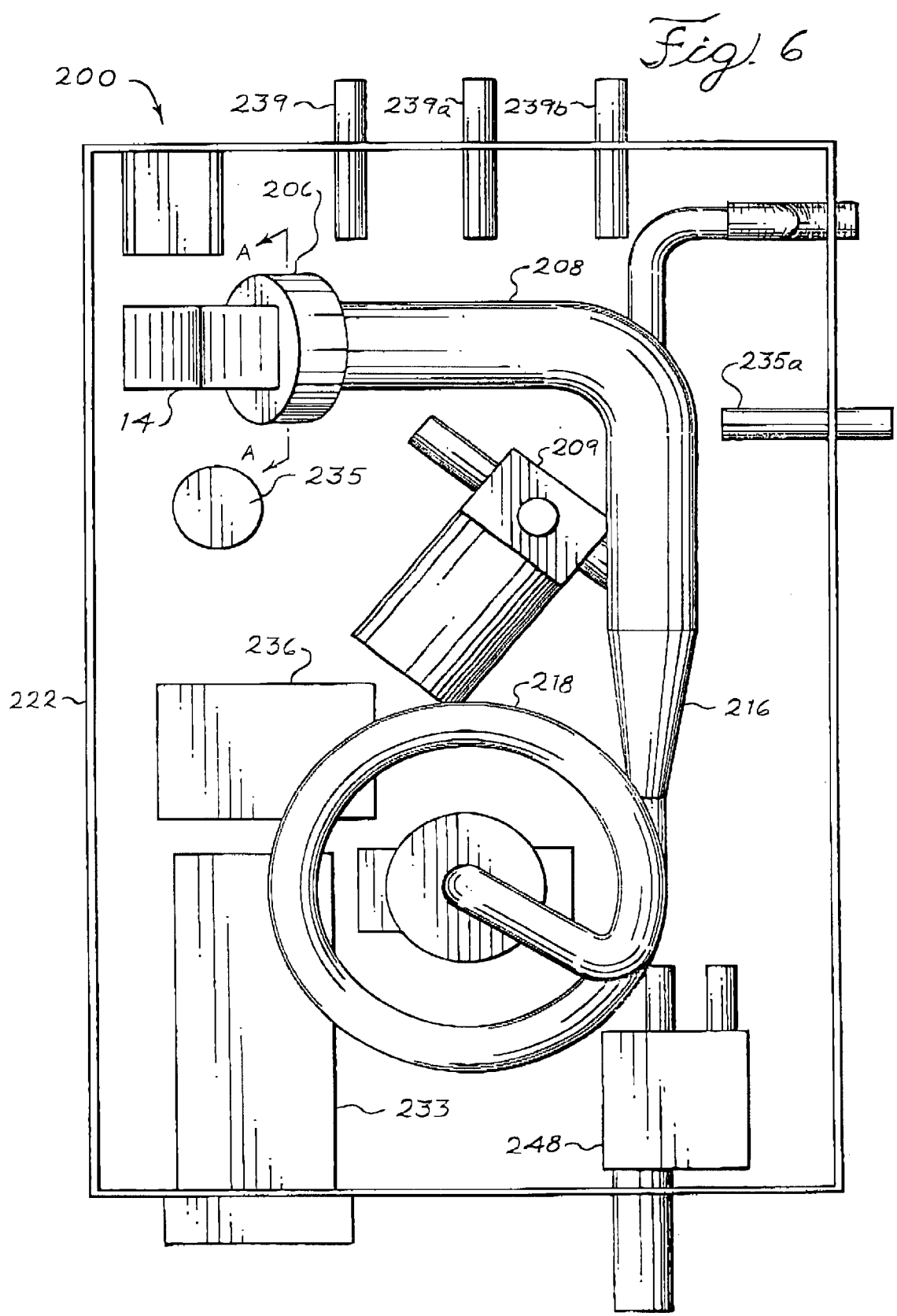
FIG. 6 is a top isometric view of the configuration for a low temperature adaptor.

Isometric views of the low temperature adaptor according to one embodiment of the invention are illustrated in FIGS. 5–6. The low temperature adaptor 200 has a nebulizer 14. The nebulizer 14 is the same as the nebulizer previously described. The nebulizer 14 may either be the nebulizer 14 removed from the evaporative light scattering device 10 before attaching the low temperature adaptor, or it may be a second nebulizer. The nebulizer 14 is connected to a nebulization chamber 208 by nebulizer union 206. Details concerning the manner of attachment of the nebulizer 14 to the nebulizer union 206 are discussed below with reference to FIGS. 8a and 8b. The nebulizer union 206 is preferably made from stainless steel and is friction fit to the nebulization chamber 208 by O-ring 246. The nebulization chamber 208 has a sink trap drain 212. A tapered connector 216 attaches the nebulization chamber 208 to coil 218. The connector 216 is preferably made from stainless steel and is welded to the chamber 208 and coil 218. The chamber 208 and coil 218 are also preferably made from stainless steel. The coil 218 is preferably ½ inch or 1 inch in diameter. The foregoing pieces are preferably contained in housing 222.

A gas filter in-line 226 is preferably provided for supplying the sweep gas to the nebulizer union member 206 as described below. A back pressure line 227 is also preferably provided to flow chromatography effluent away from the nebulizer 14 to waste when chromatography effluent exceeds a pre-determined pressure limit. The coil 218 exits housing 222 to flow the nebulized chromatography effluent to the evaporative light scattering detection device via connection tube 260 described herein. Finally, the housing 222 also preferably includes power module 232, temperature controller 233, sweep gas regulator 209, back pressure regulator 235, sold state relay 236, and mass flow controller 248.

Sweep gas regulator 209 regulates the flowrate of the sweep gas introduced to the nebulizer 14 from a sweep gas source (not shown). Preferably, the sweep gas is selected from the same gas as the nebulizing gas. Most preferably, the sweep gas is nitrogen. Suitable tubing (not shown) provides a gas connection between the sweep gas regulator 209 and the nebulizer union 206. Back pressure regulator 235 is in fluid connection with nebulizer 14 by stainless steel. If the back pressure exceeds a pre-determined level, the back pressure regulator diverts chromatography effluent flow from nebulizer 14 through back pressure regulator 235 to back pressure waste line 235a (not shown in its entirety). Back pressure waste line 235a exits the low temperature adapter housing 222 and flows the chromatography effluent to waste. A preferred back pressure regulator is a diaphragm back pressure regulator available from the assignee of this application, ALLTECH ASSOCIATES, INC. The solid state relay 236 is in electrical connection with the heat tape 228 affixed to nebulization chamber 208 and coil 218 and temperature controller 233. The solid state relay turns the heat tape "on" and "off" in response to the temperature controller 233. A preferred temperature controller is a PID action, TC input available from WATLOW, as part no. 965A3CA000BR. A preferred solid state relay is available from NEWARK, as part no. 27F329. The mass flow controller 248 controls the flow of nebulizing gas to the nebulizer 14. The mass flow controller 248 is in gas communication with the nebulizer 14 and the nebulizing gas source (not shown) by suitable tubing, as for example TEFLON tubing. A preferred mass flow controller is as previously described with respect to the evaporative light scattering device 10.

The low temperature adapter preferably uses one gas source for both the nebulizing gas and the sweep gas. Preferably, the gas (which is preferably nitrogen) enters the low temperature adapter housing 222 at "gas in" line 239. After entering the low temperature adapter, the gas is split into two gas streams. The first stream, the sweep gas is flowed to a sweep gas filter (not shown) for removing impurities from the sweep gas. The sweep gas is then flowed from the filter to the sweep gas regulator 209 and nebulizer 14, respectively. The second stream, the nebulizing gas, is flowed out of the low temperature adapter housing 222 via "ELSD out" line 239a. The nebulizing gas is flowed into the evaporative light scattering device 10 where it is filtered by nebulizing gas filter 30 in the scattering device 10. After filtering to remove impurities, the nebulizing gas is flowed through mass flow sensor 36 in the scattering device 10 and back to the low temperature adapter through "ELSD in" line 239b to mass flow controller 248 and nebulization chamber 208, respectively.

Figure 7:
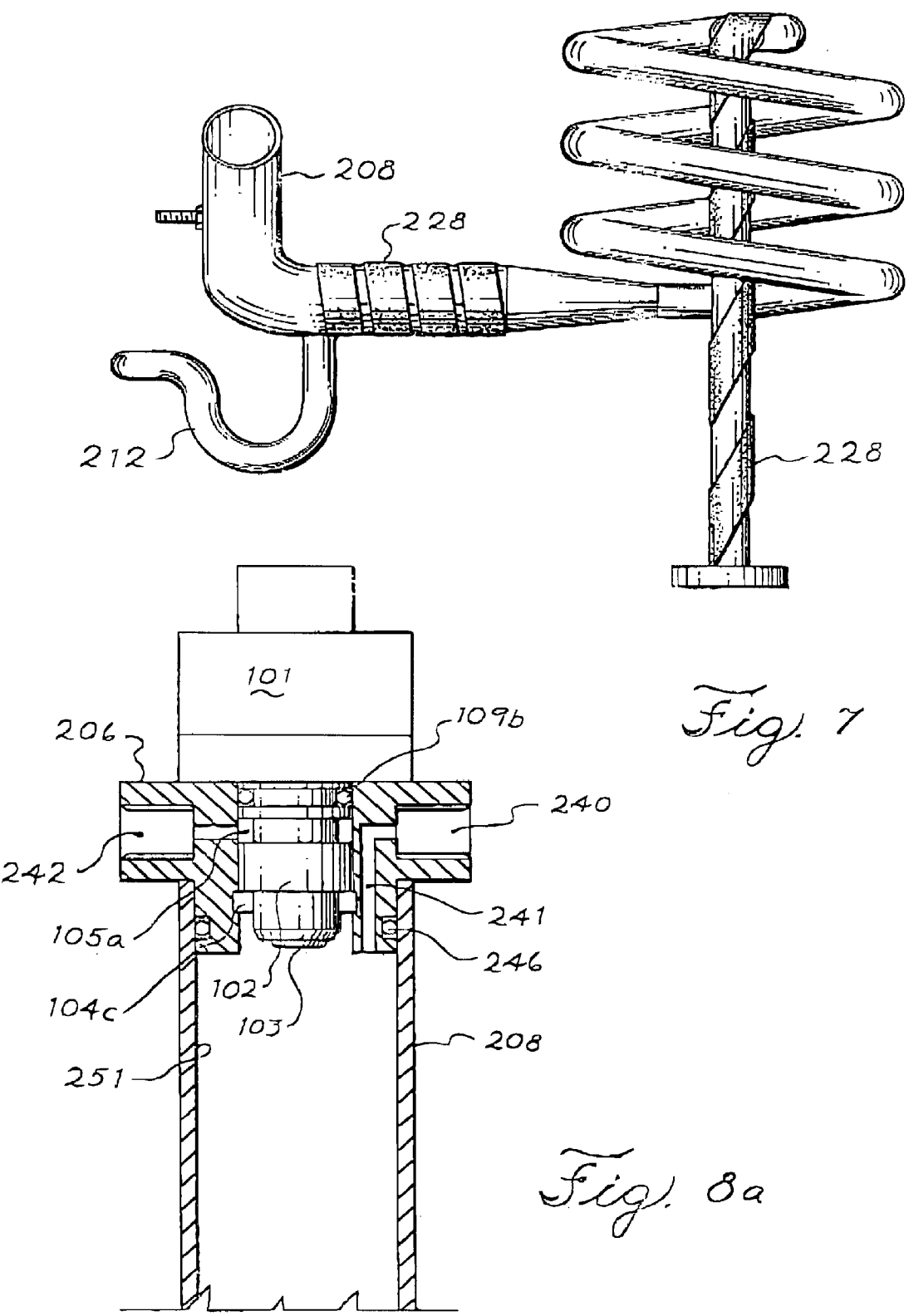
FIG. 7 is a perspective view of the coil and nebulization chamber of the low temperature adaptor.

With reference to FIG. 7, heat tape 228 is preferably wrapped around the nebulization chamber 208 and the coil 218 at predetermined intervals. By varying the amount of heat tape on the nebulization chamber 208 and the coil 218, a heat application gradient may be established. Preferably, heat is applied at a higher rate at the nebulization chamber 208 than at the coil 218. The majority of evaporation takes place in the nebulization chamber, and the surface area per unit length in the nebulization chamber 208 is greater than in the coil 218. If there is not enough heat in the nebulization chamber, a greater percentage of the mobile phase will pass through the chamber and ultimately to the optical cell for detection. This will result in an unstable baseline and hinder detection of the sample. On the other hand, if there is too much heat applied at the coil 218, there is a risk of evaporating sample which will reduce the amount of sample detected. By asymmetrically applying the heat tape at the nebulization chamber 208, and the coil 218, more heat may be delivered to the nebulization chamber 208 than to the coil 218 using the same heat source. When ½ inch coil is used, it is preferred to leave ½ to ¾ inch spacing between the heat tape. When 1 inch coil is used, it is preferred to leave ⅛ inch spacing between the heat tape. Most preferably, the amount of heat tape per surface area is greater in the nebulization chamber 208 than in coil 218. Most preferably, the ratio of applied heat per unit surface area in the nebulization chamber 208 to the coil 218 is about 1:1 to about 3:1 and most preferably about 1.7:1. The heat tape 228 is preferably cut from ½ inch width H-series heat tape. Preferred heat tape is available from CLAYBORN, under part no. J-16-4. The heat tape is in electrical connection with power module 232 in the low temperature adaptor housing 222 (see FIG. 5).

Figure 8:
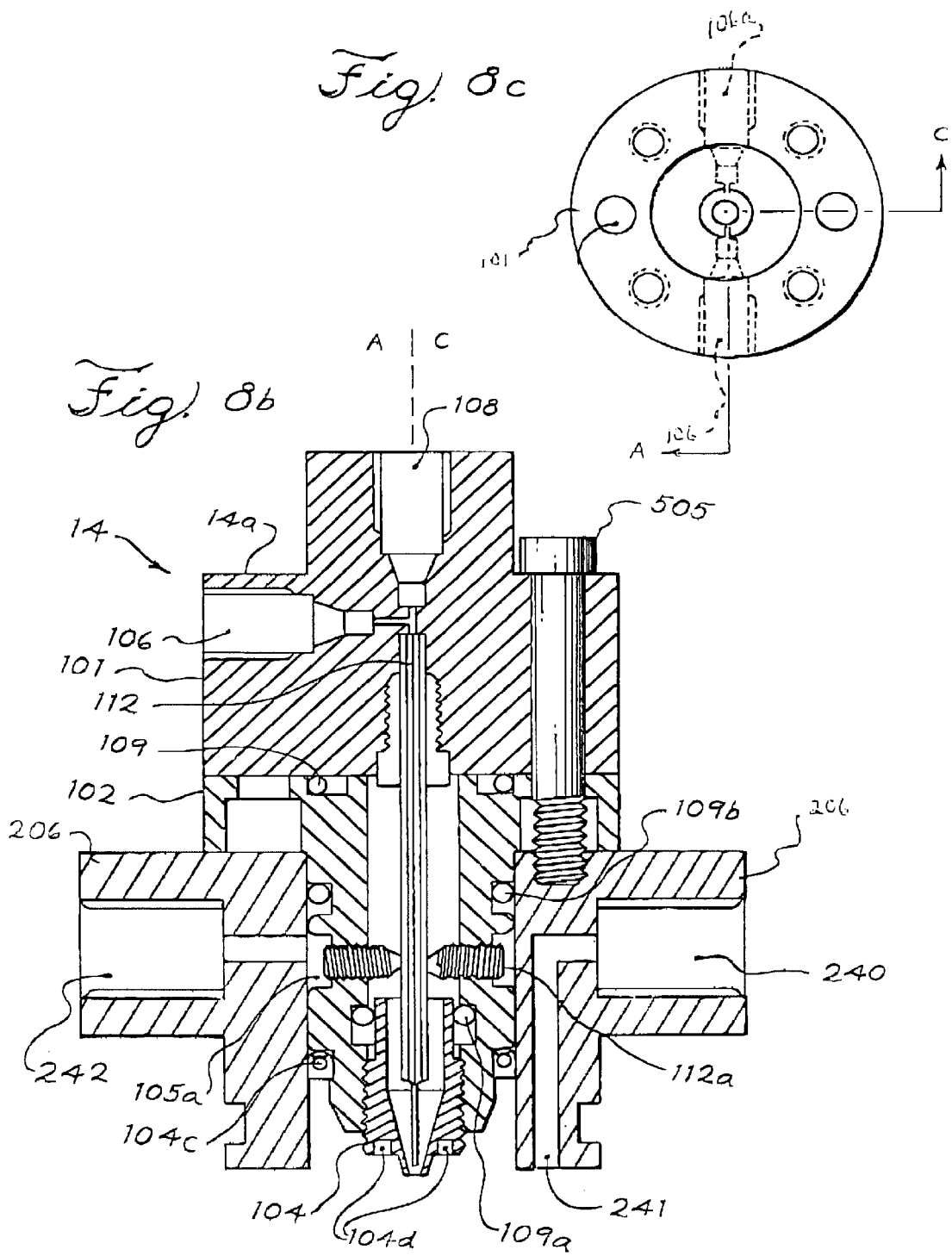

FIGS. 8a and 8b further illustrates the connection between the nebulizer 14 and the nebulizer union 206 of the low temperature adaptor. The nebulizer consists of tee nozzle 101, nebulizer body 102 and tip 104 and is as previously described with reference to FIGS. 3, 3a, and 3b. Chromatography effluent is delivered to tee nozzle 101 by the same means previously described with respect to connector 12 and chromatography effluent line 12a. The union 206 has a sweep gas port 240 and sweep gas channel 241, which are in gas communication with nebulization chamber 208. Port 240 and channel 241 are for introducing sweep gas to the nebulization chamber 208. Port 240 is in gas communication with sweep gas regulator 209 (see FIGS. 5 and 6). The sweep gas is preferably introduced into the same plane as the tip of the nebulizer needle and parallel to the nebulizing gas. The purpose of the sweep gas is to assist in evaporating the mobile phase and to provide a way of controlling the evaporation rate without affecting nebulization and particle size distribution in the mobile phase. The nebulizer union 206 further includes nebulizing gas port 242 which introduces nebulizing gas to the nebulizer as previously described with respect to FIGS. 3, 3a, and 3b. Nebulizing gas flow rate is controlled by any suitable gas valve or valving arrangement. Preferably, the nebulizing gas is delivered from the same nebulizing gas source as used by the evaporative light scattering detection device. Seal 246 provides a gas tight seal between the inside wall 251 of nebulization chamber 208 and nebulizer union 206. This seal is preferably EPDM rubber seal available from McMASTER CARR, Chicago, Ill., as part no. 9557K19. Nebulizer 14 is removably attached to union 206 by screw 505.

Figure 9:
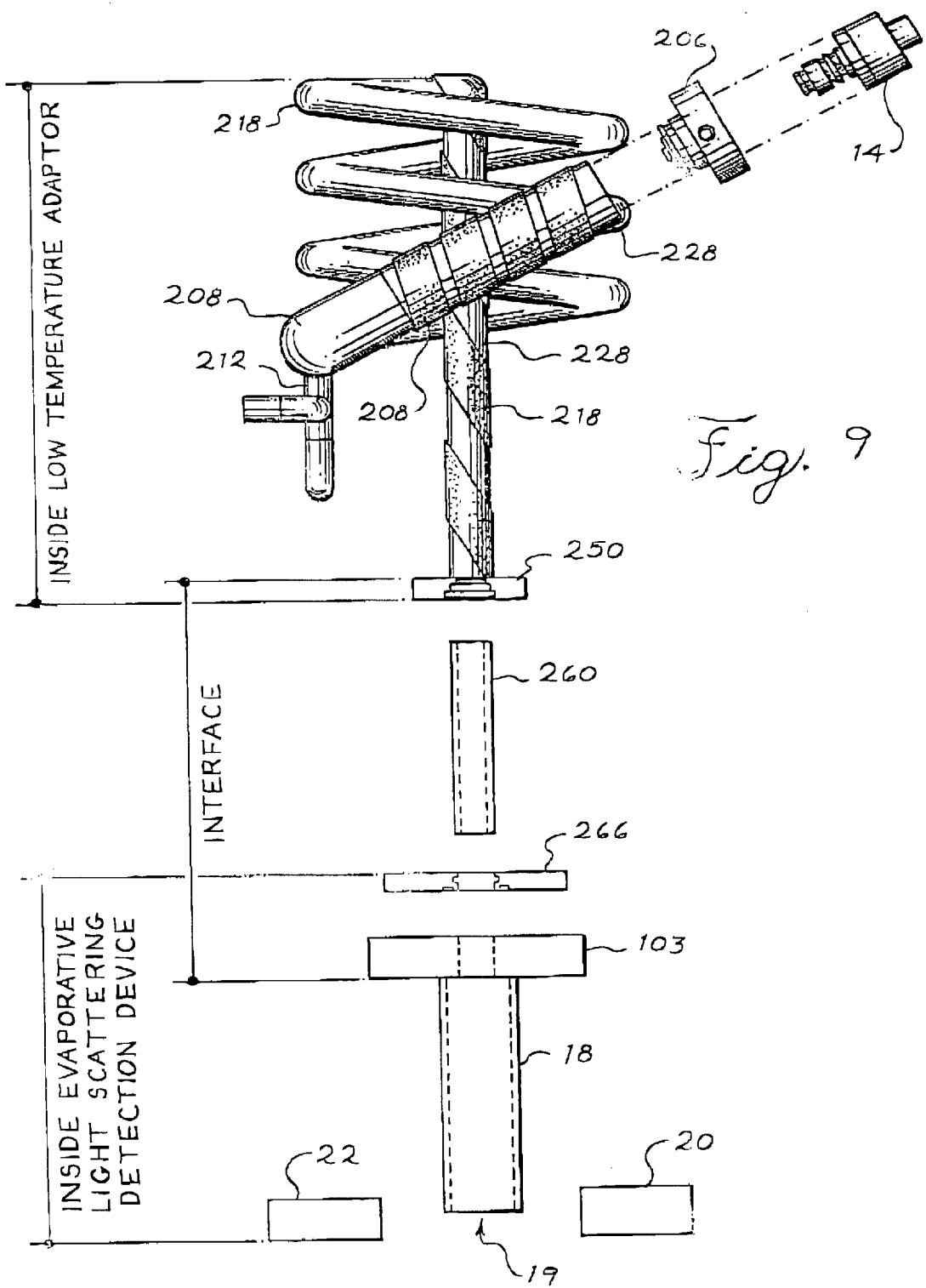
FIG. 9 is a diagram depicting sample flow through the low temperature adaptor and the evaporative light scattering device.

FIG. 9 illustrates the flow path and method of operation when the low temperature adaptor is used in conjunction with the evaporative light scattering device. The chromatography effluent is flowed through a nebulizer 14 and nebulizer union 206. The nebulized chromatography effluent is flowed to nebulization chamber 208 where the larger droplets of the mobile phase collide with the inside walls of the chamber 208 and are flowed to waste via sink trap 212. By removing the larger particles in the chromatography effluent, a smaller droplet size distribution is created and the temperature required to evaporate the remaining droplets of the mobile phase is reduced. Hence the name "low temperature adaptor." To avoid widely fluctuating temperatures that may adversely affect reproducibility, the temperature of the nebulization chamber 208 is precisely controlled with the heat tape 228. Evaporation of the mobile phase begins in the nebulization chamber 208. The "split" nebulized chromatography effluent is then flowed through heated coil 218 where evaporation of the mobile phase continues. Because of the smaller particle size distribution in the mobile phase, the evaporation temperatures used in the coil 218 are lower than if the chromatography effluent was not first split in the nebulization chamber 208. By operating at a lower evaporation temperatures, the low temperature adaptor improves the sensitivity of the system to semi-volatile samples. The sample, which has not been evaporated, is then flowed through connection tube 260 and drift tube assembly 18, respectively, to detection zone 19.

Figure 10:
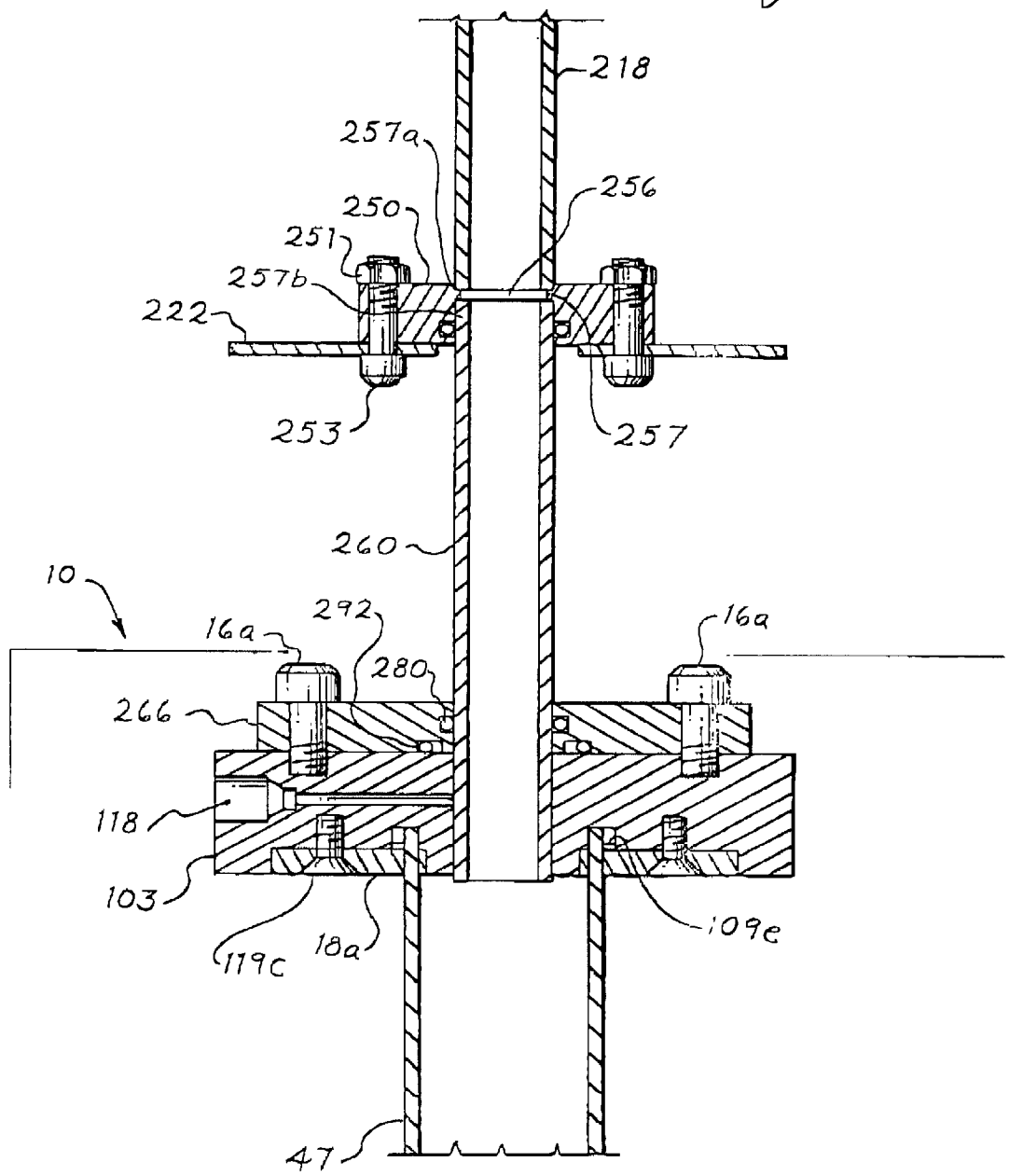
FIG. 10 is a cross-section view along line D—D of FIG. 9 showing the connection between the low temperature adaptor, connection tube and evaporative light scattering device.

FIG. 10 illustrates the interface between the low temperature adaptor and the evaporative light scattering device. The coil 218 is secured to the bottom of housing 222 for the low temperature adaptor by coil connection plate 250. The connection plate 250 is welded to the coil 218 and is removably secured to the housing 222 by hex head nuts 251 and socket head cap screws 253. A channel 256 extends along a vertical axis through connection plate 250. A shoulder 257 is positioned in channel 256. A lower end of coil 218 abuts against one side 257a of shoulder 257. A connection tube 260 is inserted into channel 256 until it abuts against the opposite side 257b of shoulder 257. An O-ring 261 is provided to form a gas and liquid tight seal between connection tube 260 and the inside wall of channel 256 of connection plate 250. O-ring 261 is preferably EPDM rubber such as McMASTER CARR part no. 9557K2-018.

The connection tube 260 (which is preferably made from stainless steel) is in fluid communication with tube 47 of drift tube assembly 18 of the evaporative light scattering device 10. In particular, the housing for the evaporative light scattering device 10 has a recess 10a. The recess 10a is exposed by removing a removable cover cap (not shown) from the housing of evaporative light scattering device 10. The removable cover cap is configured to cover the recess 10a when the system is in the single flow configuration and, therefore, the low temperature adaptor is not on-line. Sitting in recess 10a is the drift tube assembly 18. Attached to the drift tube assembly 18 is drift tube cap 118a. The nebulizer adaptor 103 is removably secured to the drift tube cap 118a by screws 119e as previously described. Nebulizer adaptor 103 has screw channels 103b for receiving screws 16a. Connection tube plate 266 is, therefore, removably secured to nebulizer adaptor 103 by screws 16a. Connection tube plate 266 has a bore for receiving connection tube 260. Connection tube seal 280 provides a gas and liquid tight seal between the connection tube 260 and connection tube plate 266. Connection plate seal 282 provides a gas and liquid tight seal between connection tube plate 266 and nebulizer adaptor 103. Seal 280 is the same type as seal 260 and seal 282 is the same type as seal 246. As can be ascertained from comparing FIGS. 4 and 10, the low temperature adaptor may be quickly and easily attached to the evaporative light scattering device 10 by removing the nebulizer bracket 16 and nebulizer 14, and then inserting connection tube 260 through nebulizer adaptor 103, applying connection tube and connection plate seals 280 and 282, respectively, and securing screws 16a. By following these simple steps and re-routing nebulizing gas flow and the chromatography effluent flow, an evaporative light scattering detection device 10 may be quickly and easily converted between the single flow and split flow designs.

The low temperature adaptor is intended to operate at low temperatures and low nebulizing gas flow rates. The low temperature adaptor will be preferably operated in a temperature range of ambient to 100 C in 1C increments. The nebulizing gas is preferably nitrogen with a pressure range of about 45 to about 80 psig and a flow rate of (0–5 SLPM). The mobile phase flowrate is preferably about 0.1 to about 5.0 mL/min. The temperature controller is preferably a microprocessor based PID temperature controller. The mobile phase flow path is preferably made from stainless steel. The gas flowpath is preferably made from TEFLON tubing. In general, an operating temperature of about 40 C and a nebulizing gas flow rate of 1.75 SLPM is sufficient for most applications. However, to obtain maximum detector response for each application, some experimentation may be necessary to determine optimum temperature and nebulizing gas flowrate.

Temperature selection depends mainly on the volatility of the mobile phase used, but is also affected by the mobile phase flowrate. Aqueous solvents require slightly higher temperatures than organic solvents. A temperature of about 40 C is sufficient to evaporate mobile phases consisting of 100% water at flowrates up to 2.0 mL/min. and, therefore, is a good starting point. Mobile phases containing a large portion of organics may require temperatures as low as ambient (25 C). The low temperature adaptor is preferably not used with such mobile phases unless semi-volatile samples are involved. Most preferably, the lowest temperature that produces an acceptable, low noise baseline should be used for most applications. It should also be noted that the low temperature adaptor and the evaporative light scattering device should be operated at the same temperature.

The nebulizing flowrate selection will also depend on mobile phase volatility and mobile phase flowrate. Preferably, nebulizing gas flowrates will be under 2.0 SLPM, unless extremely high mobile phase flowrates are used. For low mobile phase flowrates or highly organic mobile phases, nebulizing gas flowrates may be as low as 1.0 SLPM. Most preferably, the lowest gas flowrate that produces an acceptable, low noise baseline should be used.

In general, when using non-volatile samples and organic mobile phases, the single flow evaporative light scattering device may be used. However, when switching to semi-volatile sample types, aqueous mobile phases and/or higher mobile phase flowrates, the evaporative light scattering device of the present invention may be quickly and easily converted to a split flow design as described herein.

Following are examples demonstrating how to use the invention disclosed herein. With respect to the examples using the low temperature adapter, unless otherwise stated, nitrogen sweep gas was used at 2 SLPM. In the examples, heat tape was affixed to the coil and nebulization chamber such that the amount of heat tape on the nebulization chamber per unit service area was 1.7 times greater than that affixed to the coil.

EXAMPLES

Example 1

Figure 11:
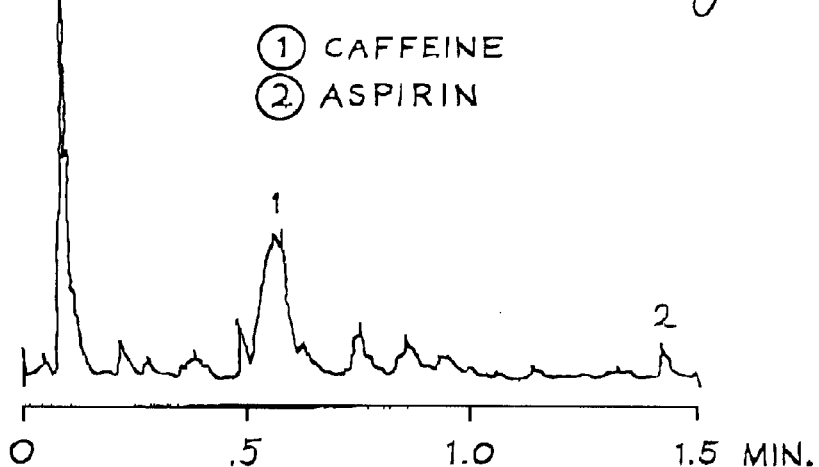
FIGS. 11–21 are chromatograms demonstrating the use of the evaporative light scattering detection device and low temperature adaptor disclosed herein.
Figure 12:
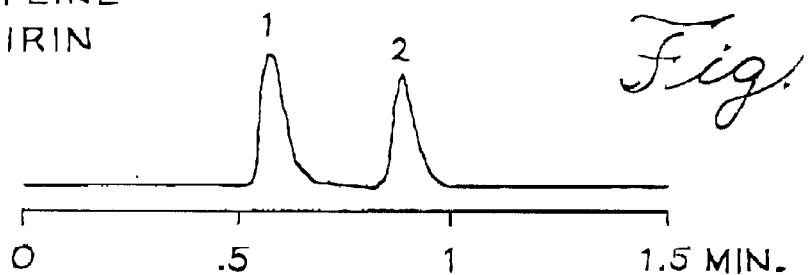

FIGS. 11 and 12 demonstrate the improved baseline stability obtained when using the low temperature adaptor (LTA) in combination with the evaporative light scattering detection (ELSD) device with a highly aqueous mobile phase. When highly aqueous mobile phases are used for the separation, higher drift tube temperatures are needed. The LTA permits effective detection of lower evaporation temperatures. FIG. 11 is a chromatogram of the ELSD alone. FIG. 12 is a chromatogram of the LTA/ELSD combination. The separation column was an Econosphere C18, 3 µm, 30×4.6 mm; the mobile phase was methanol: water: acetic acid (38:62:1); the flowrate 1.5 mL/min; sample size was 0.2 mg/mL caffeine, 0.8 mg/mL aspirin. With respect to FIG. 11, drift tube temp. 95° C., 20 µL loop, nebulizing nitrogen flow rate 3.70 SLPM. With respect to FIG. 12, drift tube temp. 50° C.; nitrogen flow 2.5 SLPM; nebulizer chamber temp. 38° C.; coil temp. 60° C.; nitrogen sweep gas flow 3 SLPM.

Example 2

Figure 13:
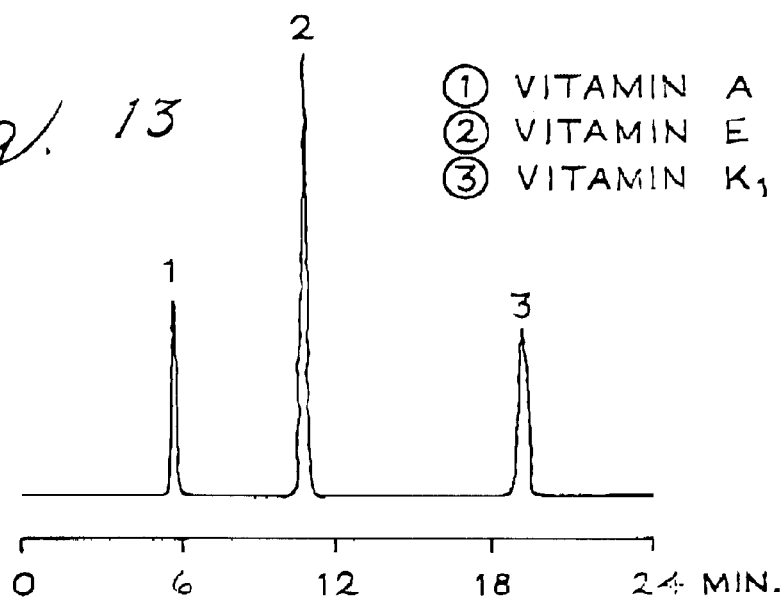
Figure 14:
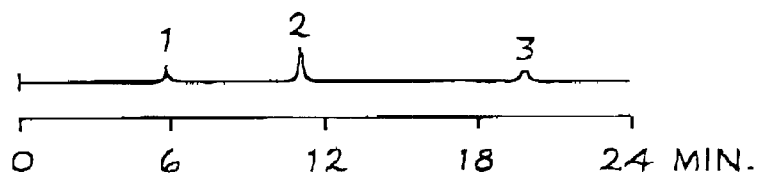

The ELSD alone is preferred for non-volatile samples or organic mobile phases. The ELSD alone is preferred when analyzing non-volatile compounds or when using organic mobile phases. FIGS. 13 and 14 demonstrate this. Organic mobile phases evaporate easily, reducing operating temperatures so that sample integrity is preserved. When using the ELSD alone, all of the sample enters the optical cell, maximizing response. With respect to FIGS. 13 and 14, separation was by HPLC. Column was Adsorbosphere C18, 5 µm, 250×4.6 mm. Mobile phase was methanol: acetonitrile (97:3); the sample size was 20 µL injection loop, mobile phase flowrate 1.0 mL/min. With respect to FIG. 13, the drift tube temp. was 70° C. and nebulizing nitrogen flow was 2.00 SLPM.

Example 3

Figure 15:
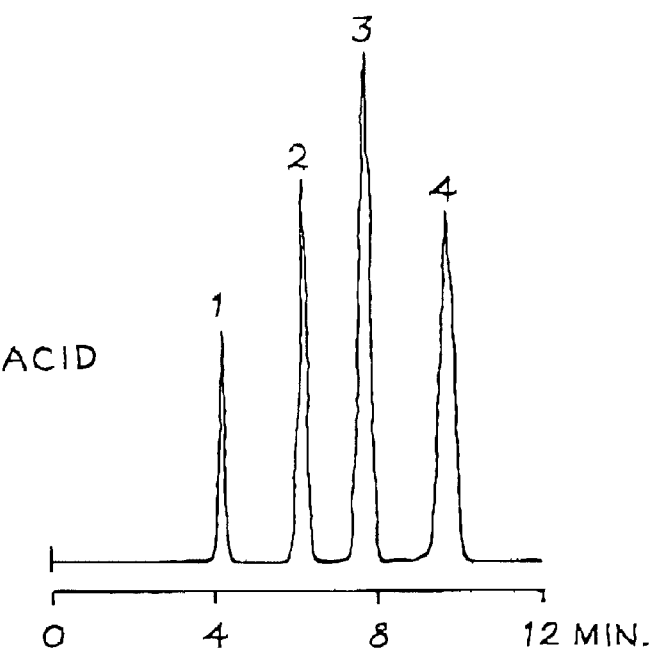
Figure 16:
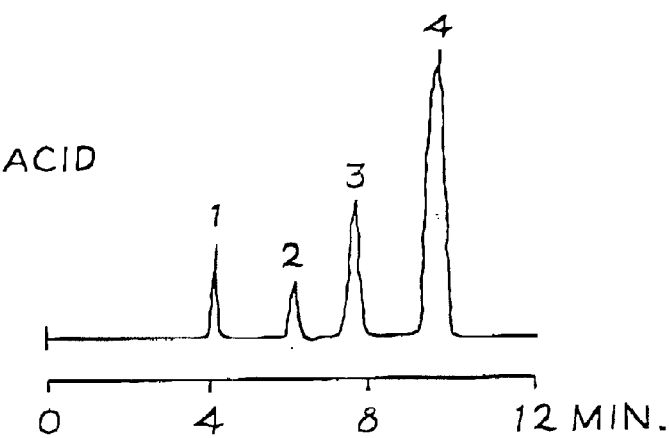

The ELS/LTA combination is preferred with semi-volatile samples. The LTA lowers the ELSD's operating temperature, eliminating semi-volatile sample loss to evaporation. This preserves sample integrity and maximizes response. This is demonstrated by FIGS. 15 and 16. FIG. 15 is a chromatogram of the ELSD/LTA combination and FIG. 16 is a chromatograph of the ELSD alone. Separation was by HPLC. Column was Alltima C18-LL, 5 µm, 250×2.1 mm. Mobile phase was a gradient of water: acetonitrile (Time (min.): % acetonitrile: 0:77, 10:80, 15:80, 20:95); flowrate 0.4 mL/min; sample size 20 µL loop. With respect to FIG. 15, drift tube and LTA temp. 30° C.; and nebulizing nitrogen flow 1.75 SLPM. With respect to FIG. 16, drift tube temp. 65° C., and nebulizing nitrogen flow 2.0 SLPM.

Example 4

Figure 17:
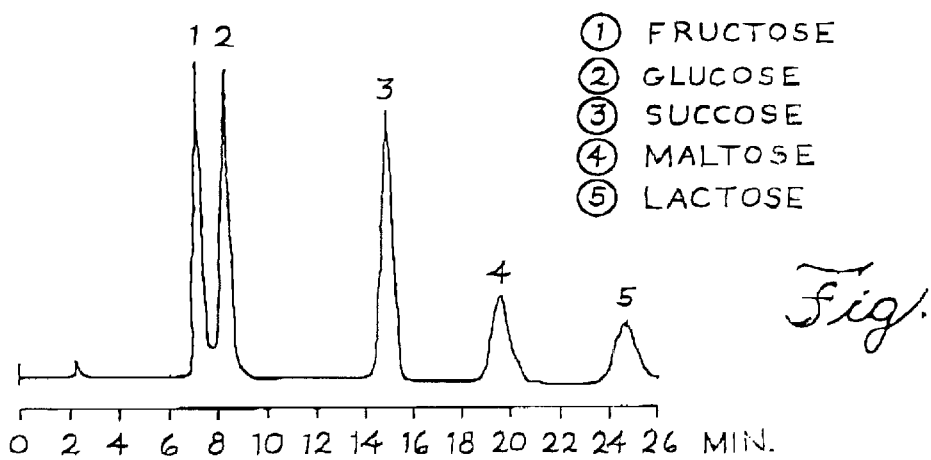

The ELSD delivers a stable baseline and excellent sensitivity for a simple sugar separation. Because carbohydrates are non-volatile and the mobile phase is mostly organic, the ELSD alone is preferred. FIG. 17 demonstrates this. The separation was by HPLC. Column was Absorbosphere, $NH_2$ 250 mm×4.6 mm, sample size was 1 mg sugar standards/ml, mobile phase. Acetonitrile: water (85:15), flowrate 1.5 mL/min., drift tube temp. 90° C., nebulizing nitrogen flow 2.20 SLPM.

Example 5

The ELSD with the LTA detects corn syrup oligomers under gradient conditions. The ELSD/LTA combination is preferred for this application because of the high flowrate and highly aqueous mobile phase. The ELSD/LTA combination maintains a stable baseline during the gradient.

Example 6

Dimethicone analysis using the ELSD combined with non-aqueous reversed phase gradient elution achieves good resolution and detection sensitivity. Because dimethicone is a large non-volatile molecule and the mobile phase is 100% organic, the ELSD alone is preferred.

Example 7

Figure 18:
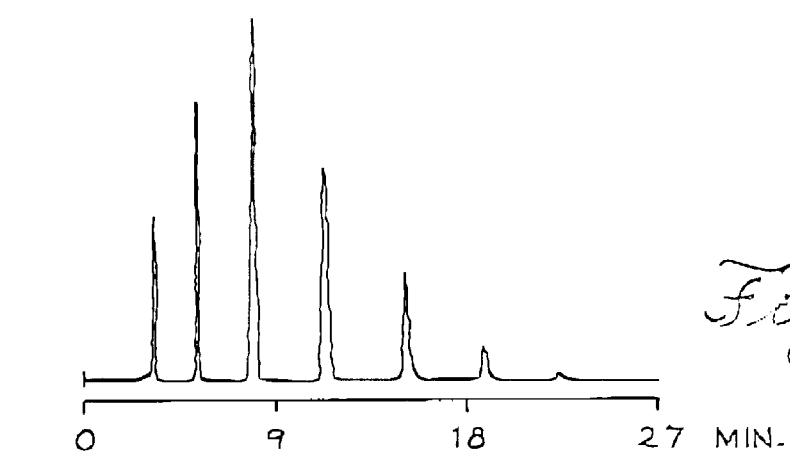

The LTA maximizes sensitivity in the analysis of PEG 200. The LTA reduces the ELSD's operating temperature and enhances the detection sensitivity of this small, semi-volatile compound. Thus, FIG. 18 is a chromatogram demonstrating the preferred results with the ELSD/LTA combination. Separation by HPLC. Column was Econophere C8 5 micron 250×4.6 mm, mobile phase water: methanol gradient (Time (min): % methanol: 0:15, 25:40, 35:40), flowrate 1.0 mL/min., sample size 1 mg/mL, drift tube and LTA temp. 30° C., nebulizing nitrogen flow 1.75 SLPM, and sweep gas 2.5 SLPM.

Example 8

Figure 19:
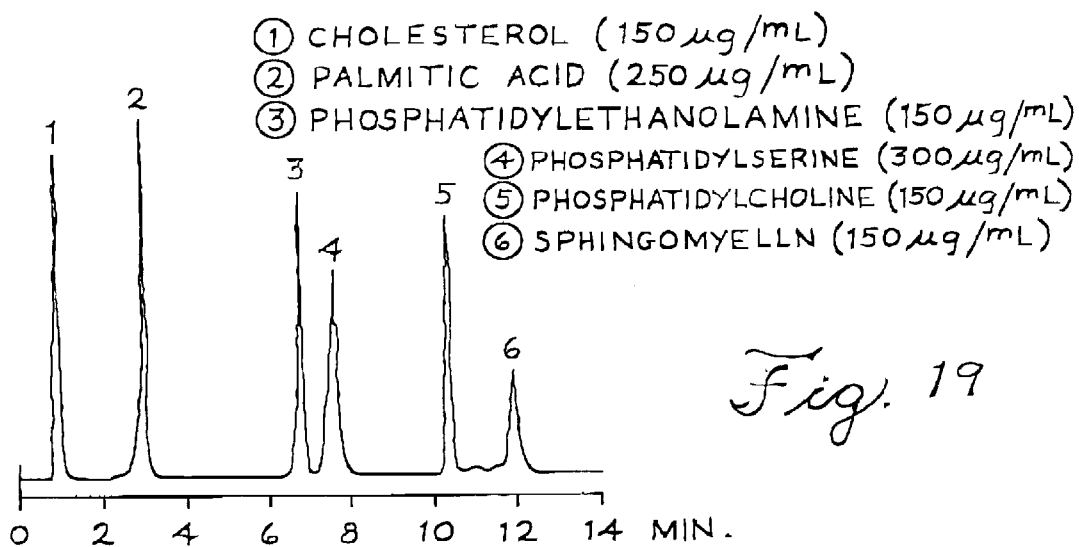
Figure 20:
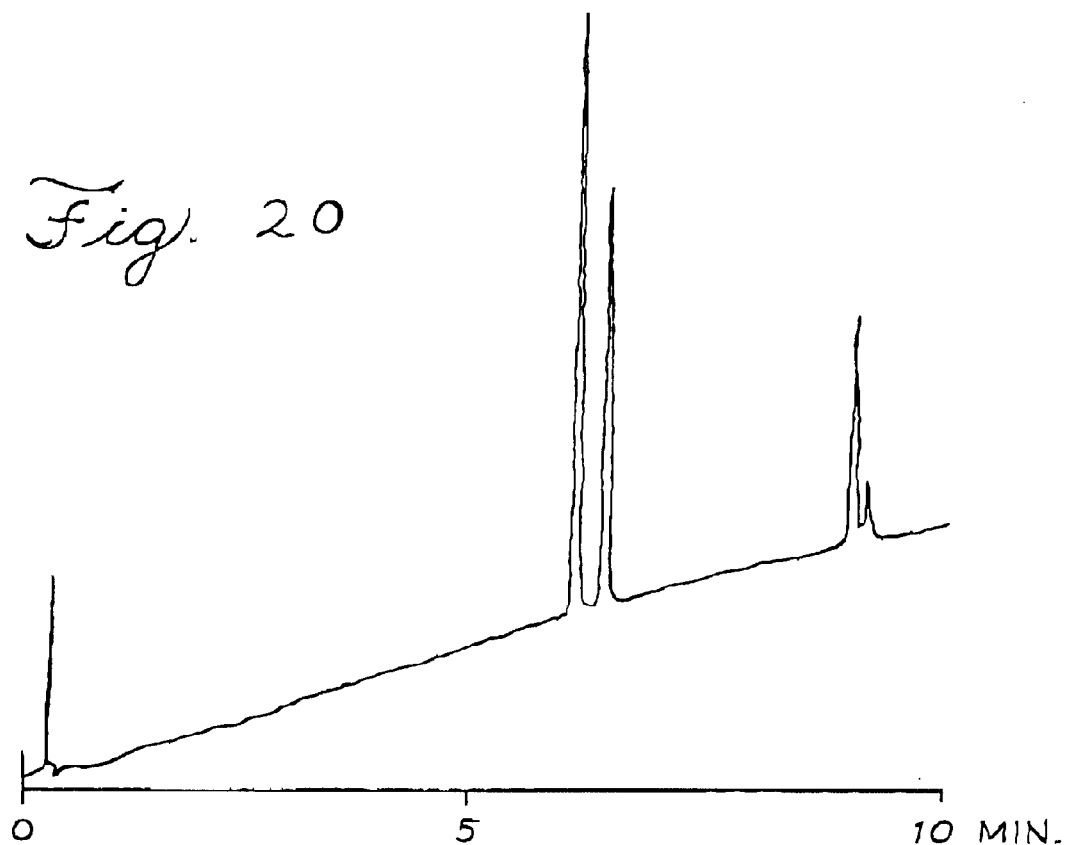

The ELSD alone is preferred for samples such as phospholipids. This configuration is ideal for normal phase applications. FIG. 19 demonstrates this. The separation was by HPLC. Column was Allsphere Silica, 3 μm, 100×4.6 mm, mobile phase gradient of IPA: Hexane: Water (Time (min.): % IPA: % Hexane: % Water: 0:58:40:2; 7:52:40:8; 15:52: 40:8, flowrate 1.25 μL/min., column temp. ambient; drift tube temp. 65° C., nebulizing nitrogen flow 2.0 SLPM.

Example 9

The LTA enhances detector sensitivity in the analysis of underivatized low-chain fatty acids. The LTA substantially lowers the ELSD's operating temperature, preventing sample loss to evaporation. A chromatogram using the preferred combination of the ELSD/LTA is shown in FIG. 19. The separation was by HPLC. Column was Alltima C18, LL, 5 mm (250×2.1 mm), sample size 20 μL injection loop, mobile phase, gradient water: acetonitrile (time (min.): % of acetonitrile): 0:77, 5:80, 10:80, 20:95; flowrate 0.4 ml/min., drift tube and LTA temp. 30° C., and nebulizing nitrogen flow 1.25 SLPM.

Example 10

Large macrolides are not subject to sample evaporation, therefore the ELSD alone is preferred.

Example 11

Figure 21:
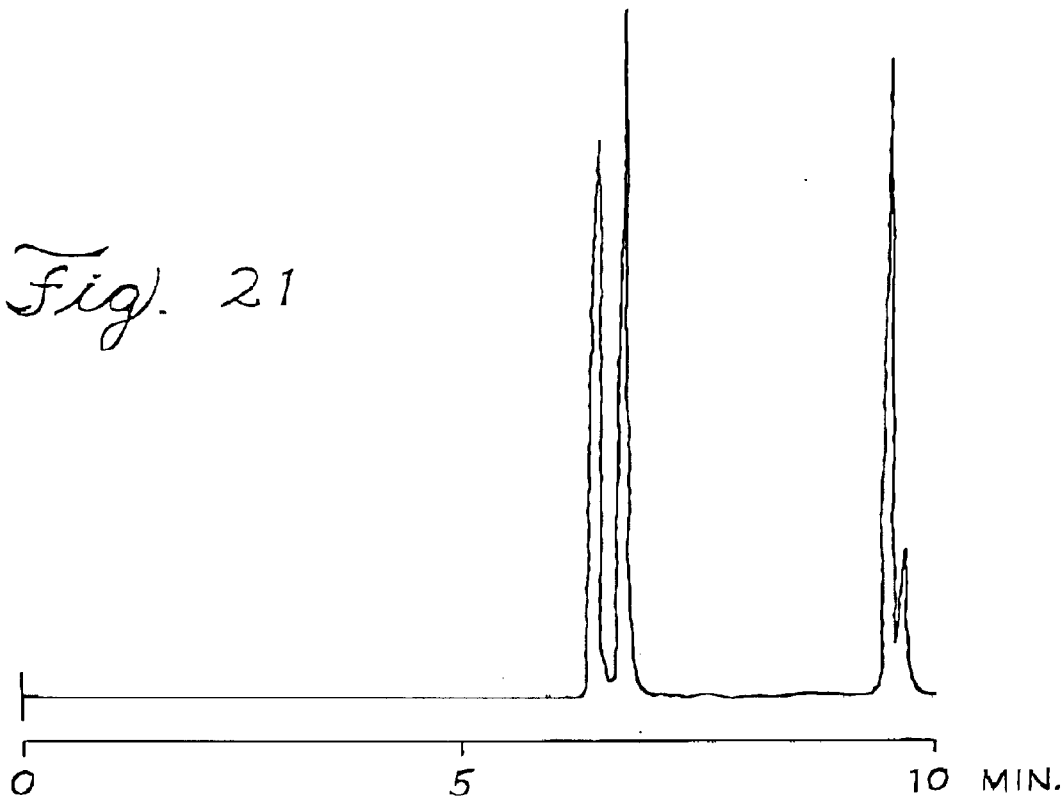

Assessing lead drug purity is preferred using the ELSD/LTA combination compared to UV because the ELSD's signal closely reflects the sample's mass balance. The LTA accepts high flowrates and operates at low temperatures for the extreme gradient conditions used during high-throughput screening. This is demonstrated by FIGS. 23 and 24. FIG. 23 is a chromatogram from using UV detection. FIG. 21 is a chromatogram generated by the preferred ELSD/LTA combination. The separation was by HPLC. Column was Alltima C18, 5 mm, 50×2.1 mm, mobile phase gradient of water (0.1% formic acid): acetonitrile (0.1% formic acid) (time (min): % acetonitrile): 0:5, 10:95, 11:95; flowrate 0.5 mL/min., column temp. 40° C. With respect to FIG. 23, detection by UV at 220 nm. With respect to FIG. 24, LTA drift tube and LTA temp. 30° C., and nebulizing nitrogen flow 1.75 SLPM.

We claim:

1. A method for quickly converting from a single-flow configuration to a split-flow configuration of evaporative light scattering detection thereby providing increased ability to detect different sample types in different mobile phases, the method comprising:

providing an evaporative light scattering detection device in the single-flow configuration comprising a nebulizer in fluid communication with one end of a drift tube, a light source and a detector; and converting to a split-flow configuration by removing the nebulizer and connecting a low temperature adaptor such that the low temperature adaptor is in fluid communication with the drift tube, the low temperature adapter comprising a low temperature adapter nebulizer, a nebulization chamber in fluid communication with the low temperature adapter nebulizer and the drift tube, wherein in the nebulization chamber at least a portion of a mobile phase carrying sample components is evaporated and a portion of the mobile phase is not evaporated, the nebulization chamber further comprising a sink trap in fluid communication with the nebulization chamber for removing mobile phase that is not evaporated in the nebulization chamber.

2. The system of claim 1 wherein the low temperature adapter has a sweep gas channel for introducing sweep gas into the nebulization chamber.

3. The system of claim 1 wherein heat tape is affixed to the nebulization chamber of the low temperature adaptor at pre-determined intervals.

4. The method of claim 1 wherein the nebulizer and the low temperature adapter nebulizer are the same.

5. The system of claim 4 wherein heat tape is affixed to the coil of the low temperature adaptor at pre-determined intervals.

6. The method of claim 1 wherein the nebulization chamber of the low temperature adapter is in fluid communication with the drift tube via a connection tube.

7. The method of claim 6 wherein the connection tube and the nebulization chamber are in fluid communication via a coil.

8. The method of claim 1 comprising the further step of converting back to the single-flow configuration by removing the low temperature adapter and attaching a nebulizer such that it is in fluid communication with the drift tube.

9. The method of claim 8 wherein the nebulizer and the low temperature adapter nebulizer are the same.

* * * * *